United States Patent
Varadarajan et al.

(10) Patent No.: US 10,874,724 B2
(45) Date of Patent: Dec. 29, 2020

(54) ENZYMATIC IMMUNOMODULATION OF SOLID TUMORS AND USES THEREOF

(71) Applicant: University of Houston System, Houston, TX (US)

(72) Inventors: Navin Varadarajan, Houston, TX (US); Irfan Naseem Bandey, Houston, TX (US)

(73) Assignee: UNIVERSITY OF HOUSTON SYSTEM, Houston, TX (US)

(*) Notice: Subject to any disclaimer, the term of this patent is extended or adjusted under 35 U.S.C. 154(b) by 0 days.

(21) Appl. No.: 15/573,013

(22) PCT Filed: May 20, 2016

(86) PCT No.: PCT/US2016/033550
§ 371 (c)(1),
(2) Date: Nov. 9, 2017

(87) PCT Pub. No.: WO2016/191283
PCT Pub. Date: Dec. 1, 2016

(65) Prior Publication Data
US 2018/0140686 A1 May 24, 2018

Related U.S. Application Data

(60) Provisional application No. 62/165,385, filed on May 22, 2015.

(51) Int. Cl.
| | | |
|---|---|---|
| *A61K 38/50* | (2006.01) |
| *G01N 33/574* | (2006.01) |
| *A61K 47/69* | (2017.01) |
| *A61P 35/02* | (2006.01) |
| *C07K 16/28* | (2006.01) |
| *C07K 16/30* | (2006.01) |

(52) U.S. Cl.
CPC .......... *A61K 38/50* (2013.01); *A61K 47/6929* (2017.08); *A61P 35/02* (2018.01); *C07K 16/2896* (2013.01); *C07K 16/30* (2013.01); *C12Y 305/04004* (2013.01); *G01N 33/57484* (2013.01); *C07K 2317/52* (2013.01); *C07K 2319/035* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | | | |
|---|---|---|---|---|
| 8,741,283 B2* | 6/2014 | Filpula | .................. | A61K 38/50 424/94.4 |
| 9,181,342 B2* | 11/2015 | Davis | ................. | C07K 16/2818 |
| 2002/0156259 A1* | 10/2002 | Conklin | ................... | C12N 9/78 536/23.2 |

FOREIGN PATENT DOCUMENTS

WO   WO 2016/061286   *   4/2016

OTHER PUBLICATIONS

Ohta et al (PNAS, 2006, 103:13132-13137).*
Ohta & Sitkovsky (Frontiers in Immunology, Jul. 10, 2014, 5:1-9).*
Ohaegbulam et al (Trends in Molecular Medicine, Jan. 2015, 21:24-33).*
Schrama et al (2006, Nature Reviews, 5:147-159).*
Blay et al (Cancer Research, 1997, 57:2602-2605).*
Tan et al (American Journal of Pathology, 2004, 165:319-330).*
Mandapathil et al (Oncolmmunology, 2012, 1:659-669).*
Mediavilla-Varela et al (Cancer Biology & Therapy, 2013, 14:860-868).*
Antonioli, L., et al., Immunity, inflammation and cancer: a leading role for adenosine. Nat Rev Cancer, 2013. 13(12): p. 842-857.
Burnstock, G. and J.-M. Boeynaems, Purinergic signalling and immune cells. Purinergic Signalling, 2014. 10(4): p. 529-564.
Antonioli, L., et al., CD39 and CD73 in immunity and inflammation. Trends in Molecular Medicine, 2013. 19(6): p. 355-367.
Dale, N. and B.G. Frenguelli, Release of Adenosine and ATP During Ischemia and Epilepsy. Current Neuropharmacology, 2009. 7(3): p. 160-179.
Davis, S et al. "Alteration of the circulating life and antigenic properties of bovine adenosine deaminase in mice by attachment of polyethylene glycol." Clinical and experimental immunology, vol. 46,3 (1981): 649-52.
Sanmamed, M.F. et al. "Defining the optimal murine models to investigate immune checkpoint blockers and their combination with other immunotherapies." Annals of Oncology, vol. 27, Issue 7, Jul. 2016, pp. 1190-1198.
Meyts, I et al. "Deficiency of Adenosine Deaminase 2 (DADA2): Updates on the Phenotype, Genetics, Pathogenesis, and Treatment." Journal of clinical immunology, vol. 38,5 (2018): 569-578.
Pacheco, R et al. "CD26, adenosine deaminase, and adenosine receptors mediate costimulatory signals in the immunological synapse." Proceedings of the National Academy of Sciences of the United States of America. Jul. 2005, 102 (27) 9583-9588.
Zhang et al., "Discussion about Several Potential Drawbacks of PEGylated Therapeutic Proteins." Biol. Pharm. Bull. 37(3) 335-339 (2014).

* cited by examiner

*Primary Examiner* — Laura B Goddard
(74) *Attorney, Agent, or Firm* — Winstead PC

(57) ABSTRACT

In some embodiments the present disclosure pertains to a method of activating an anti-tumor immune response for the treatment of a cancer. In some embodiments, such a method comprises detecting CD26 expression in a subject in need thereof. In some embodiments, the method comprises administering to the subject a therapeutically effective amount of a composition comprising adenosine deaminase. In some embodiments, the adenosine deaminase stimulates T cell proliferation and activates maturation of macrophages or dendritic cells. In some embodiments, the present disclosure pertains to a method for targeted reduction of adenosine or deoxyadenosine in a tumor microenvironment of a solid tumor.

28 Claims, 14 Drawing Sheets

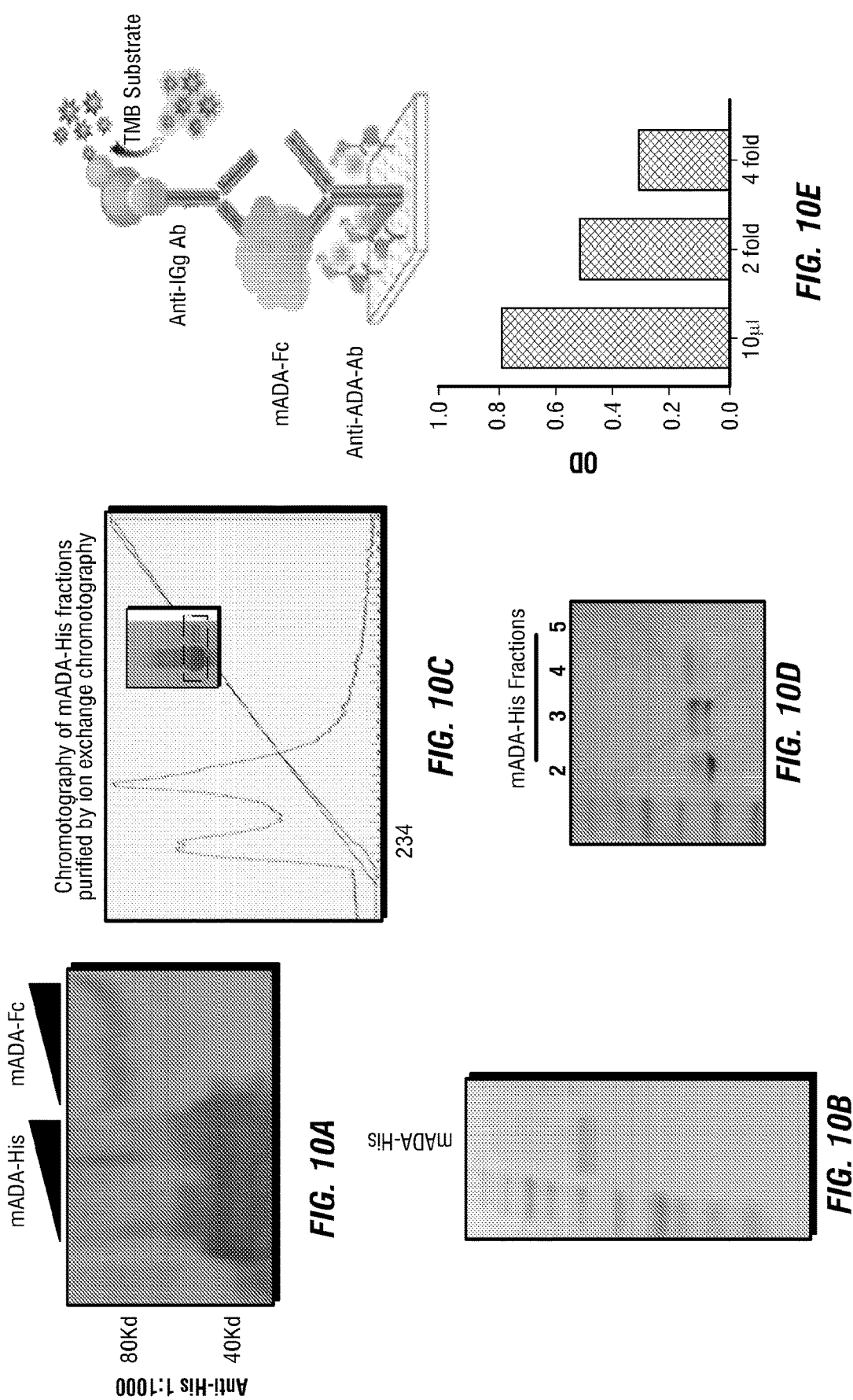

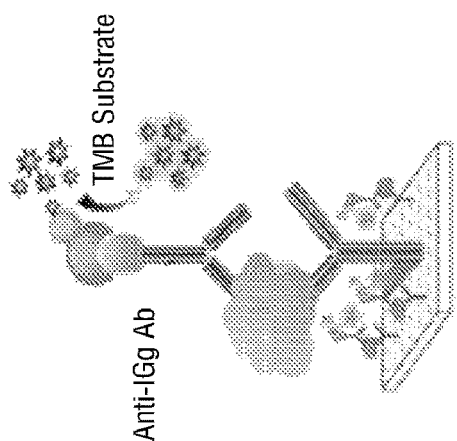
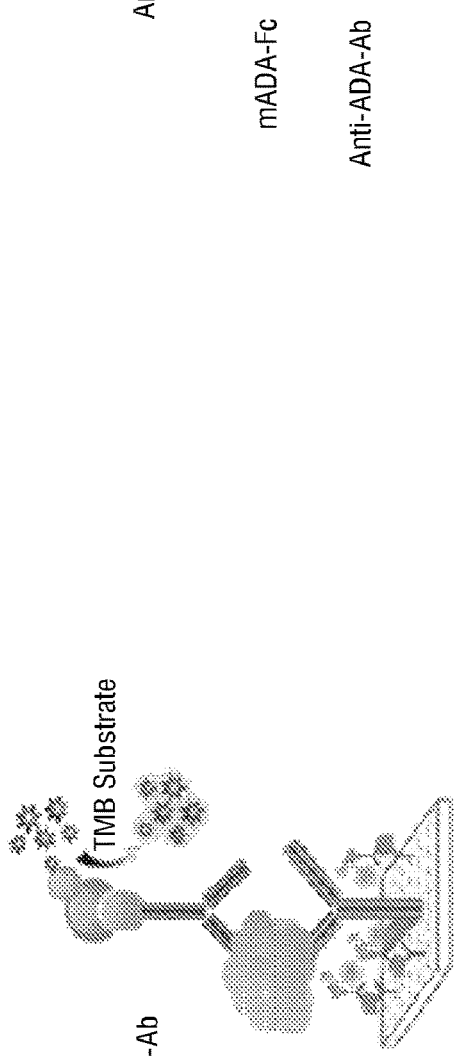
FIG. 11A
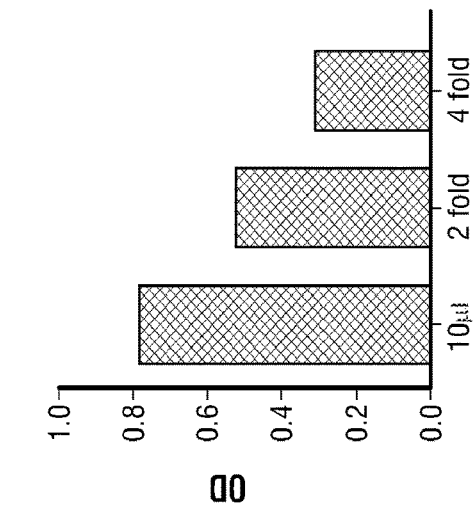
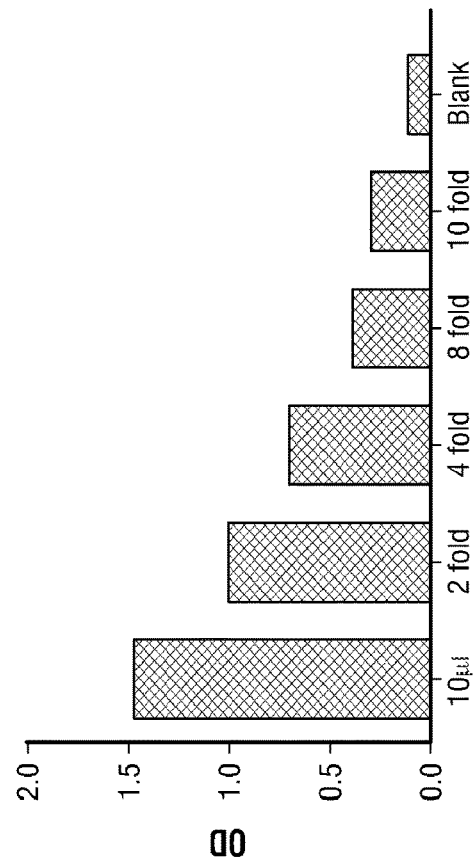
FIG. 11B

ENZYMATIC IMMUNOMODULATION OF SOLID TUMORS AND USES THEREOF

CROSS REFERENCE TO RELATED APPLICATIONS

This application claims priority to U.S. Provisional Patent Application No. 62/165,385, filed in the United States Patent and Trademark Office on May 22, 2015, the entirety of which is hereby incorporated by reference.

FIELD OF INVENTION

The invention provides new methods of treating and inhibiting tumors, and especially malignant solid tumors, by administering adenosine depleting enzymes in order to reduce tissue levels of extracellular adenosine in the tissue microenvironment.

BACKGROUND

Despite the promise of complete response with immunotherapy only a subset of patients respond to current immunotherapeutic treatments. One of the major obstacles in the treatment of solid tumors is the immunosuppressive and pro-tumor nature of the tumor-microenvironment (TME). The TME comprises of multiple elements like the extracellular matrix, soluble factors, exosomes, and cells that collectively facilitate tumor growth and help initiate metastases, inhibit host immunity, and promote resistance to both conventional and immunotherapies. Therefore, there exists a need to develop approaches that target multiple mechanisms to treat solid tumors.

SUMMARY

In some embodiments the present disclosure pertains to a method of activating an anti-tumor immune response for the treatment of a cancer. In some embodiments, such a method comprises detecting expression of at least one adenosine deaminase binding protein in a subject in need thereof. In some embodiments, the method comprises administering to the subject a therapeutically effective amount of a composition comprising adenosine deaminase. In some embodiments, the adenosine deaminase binding protein is selected from a group consisting of CD26, A(1) adenosine receptors, A(2A) adenosine receptors, A(2B) adenosine receptors, A3 adenosine receptors, and a combination thereof. In some embodiments, the anti-tumor immune response comprises stimulation of T cell proliferation and activating maturation of dendritic cells. In some embodiments, the activation of the anti-tumor immune response is in combination with administration of at least one other anti-cancer agent.

In some embodiments the present disclosure pertains to a method of activating an anti-tumor immune response for the treatment of a cancer. In some embodiments, such a method comprises detecting expression of adenosine receptors in a subject in need thereof. In some embodiments, the method comprises administering to the subject a therapeutically effective amount of a composition comprising adenosine deaminase.

In some embodiments, the present disclosure pertains to a method for targeted reduction of adenosine or deoxyadenosine in a tumor microenvironment of a solid tumor. In some embodiments, such a method comprises detecting expression of at least one adenosine deaminase binding protein in a subject in need thereof. In some embodiments, the adenosine deaminase binding protein is selected from a group consisting of CD26, A(1) adenosine receptors, A(2A) adenosine receptors, A(2B) adenosine receptors, A3 adenosine receptors, and a combination thereof. In some embodiments, the method comprises detecting expression of CD26 within the tumor microenvironment of a subject in need thereof. In some embodiments, the method comprises detecting expression of adenosine receptors within the tumor microenvironment of the subject. In some embodiments, the receptor is A(2A) adenosine receptors, A(2B) adenosine receptors, A3 adenosine receptors, or a combination thereof. In some embodiments, the method comprises administering to the subject an effective amount of a composition comprising adenosine deaminase. In some embodiments, the composition comprises a polynucleotide encoding an adenosine deaminase fusion protein. In some embodiments, the targeted reduction of adenosine within the tumor microenvironment inhibits tumor growth, metastasis, and angiogenesis.

In some embodiments, the present disclosure pertains to a method of treating a solid tumor. In some embodiments, such a method comprises detecting expression of at least one adenosine deaminase binding protein in a subject in need thereof. In some embodiments, the adenosine deaminase binding protein is selected from a group consisting of CD26, A(1) adenosine receptors, A(2A) adenosine receptors, A(2B) adenosine receptors, A3 adenosine receptors, and a combination thereof. In some embodiments, the method comprises detecting expression of CD26 within the tumor microenvironment of a subject in need thereof. In some embodiments, the method comprises detecting expression of adenosine receptors within the tumor microenvironment of the subject. In some embodiments, the adenosine receptor is A(2A) adenosine receptors, A(2B) adenosine receptors, A3 adenosine receptors, or a combination thereof. In some embodiments, the method comprises administering to the subject a therapeutically effective amount of a composition comprising adenosine deaminase. In some embodiments, the composition comprises a polynucleotide encoding an adenosine deaminase fusion protein. In some embodiments, the polynucleotide encoding the fusion protein comprises a first polynucleotide that encodes a targeting molecule a second polynucleotide that encodes adenosine deaminase. In some embodiments, the targeting molecule encoded by the first polynucleotide is specific for a tumor associated antigen expressed in the tumor microenvironment of the solid tumor. In some embodiments, such a method further comprises administering at least one other agent effective in treating the tumor. In some embodiments, the agent is a chemotherapeutic agent.

In some embodiments, the present disclosure pertains to a method of overcoming resistance to a chemotherapeutic agent in a subject in need thereof. In some embodiments, such a method comprises detecting expression of at least one adenosine deaminase binding protein in a subject in need thereof. In some embodiments, the adenosine deaminase binding protein is selected from a group consisting of CD26, A(1) adenosine receptors, A(2A) adenosine receptors, A(2B) adenosine receptors, A3 adenosine receptors, and a combination thereof. In some embodiments, the method comprises administering a therapeutically effective amount of a composition comprising an effective amount of Adenosine deaminase to the subject. In some embodiments, the composition comprises a polynucleotide encoding an adenosine deaminase fusion protein. In some embodiments, the polynucleotide encoding the fusion protein comprises a first polynucleotide that encodes a targeting molecule a second polynucleotide that encodes adenosine deaminase. In some embodiments, the targeting molecule encoded by the first polynucleotide is specific for a tumor associated antigen expressed in the tumor microenvironment of the solid tumor. In some embodiments, the subject suffers from a chemoresistant tumor. In some embodiments, the chemoresistant tumor is a triple negative breast cancer.

In some embodiments, the present disclosure relates to a method of improving the efficacy of antibody mediated immunotherapy of a tumor. In some embodiments, such a method comprises detecting expression of at least one adenosine deaminase binding protein in a subject in need thereof. In some embodiments, the adenosine deaminase binding protein is selected from a group consisting of CD26, A(1) adenosine receptors, A(2A) adenosine receptors, A(2B) adenosine receptors, A3 adenosine receptors, and a combination thereof. In some embodiments, the method comprises administering to a subject in need thereof a therapeutically effective amount of a composition comprising adenosine deaminase. In some embodiments, the subject is undergoing antibody therapy for a solid tumor.

In some embodiments, the present disclosure pertains to a method of treating a solid tumor. Such a method comprises detecting expression of at least one adenosine-dependent pathway protein in a subject in need thereof. In some embodiments, the method comprises administering to the subject a therapeutically effective amount of a composition comprising a polynucleotide encoding an adenosine deaminase fusion protein. In some embodiments, the polynucleotide encoding the fusion protein comprises a first polynucleotide that encodes a targeting molecule. In some embodiments, the polynucleotide encoding the fusion protein comprises a second polynucleotide that encodes adenosine deaminase. In some embodiments, the targeting molecule encoded by the first polynucleotide is specific for a tumor associated antigen expressed in the tumor microenvironment of the solid tumor. In some embodiment, the method is effective in inhibiting tumor growth, metastasis, and angiogenesis.

BRIEF DESCRIPTION OF THE FIGURES

FIGS. 10A-10E show purification of mADA. mADA-His and mADA-Fc were detected in the supernatant of HEK293F cells as shown by WB using Anti-His antibody (FIG. 10A). mADA-His was purified with Ni-NTA Column (FIG. 10B). The impurities were further removed using ion exchange chromatography (FIGS. 10C-10D). The purity of mADA-His was checked by loading elute on to a SDS PAGE and the gel was stained with coomassie blue (FIG. 10D). The binding efficiency of mADA-Fc to Anti IGg antibody for purification using sandwich ELISA was assessed (FIG. 10E).

FIGS. 11A and 11B show ELISA for testing the binding efficiency of purified mADA with anti-his antibody (FIG. 11A), and anti-IGg antibody (FIG. 11B).

DETAILED DESCRIPTION

Figure 1:
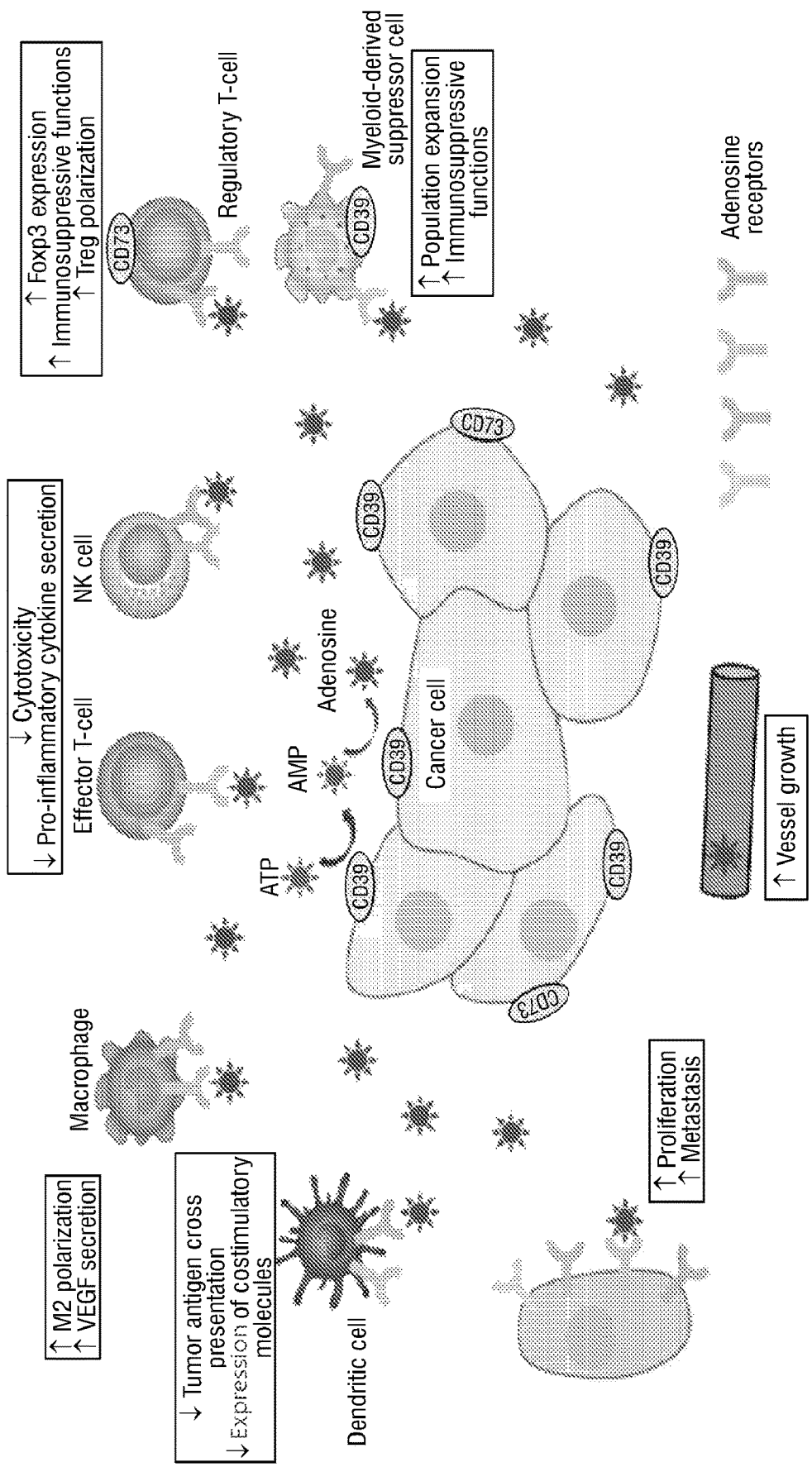
FIG. 1 depicts the many different roles of adenosine in promoting tumor progression and immunosuppression by acting through the adenosine family of receptors.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Unless defined otherwise, all technical and scientific terms used herein have the meaning commonly understood by a person skilled in the art to which the invention belongs. The following references provide one of skill with a general definition of many of the terms used in this disclosure: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ ed., R. Reigers et al. (eds.), Springer Verlag (1991); and Hale & Marham, The Harper Collins Dictionary of Biology (1991).

As used herein "therapeutically effective amount" or "an effective amount" is an art-recognized term. In certain embodiments, the term refers to an amount of a salt or composition disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

The amount of adenosine deaminase that is administered is an "effective amount" or a "therapeutically effective amount". In some embodiments, the term refers to an amount effective in activating T cells in the tumor microenvironment, such that the growth, spread, and/or angiogenesis associated with the cancer or tumor is inhibited. In some embodiments, the term refers to an amount effective in substantially reducing tissue levels of adenosine in a subject, and where such reduced tissue levels of adenosine deaminase are effective in inhibiting the growth, metastasis, and angiogenesis associated with the cancer or tumor. The cancer may be malignant or nonmalignant, and is preferably a solid tumor, e.g., a tumor such as a prostate tumor, an ovarian cancer and/or a colorectal cancer. The cancer may be leukemia.

As used herein "subject" or "individual" or "patient," may mean either a human or non-human animal, such as primates, mammals, and vertebrates.

The term, "recombinant" refers to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous (exogenous or foreign) nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, under-expressed or not expressed at all. Alternately, proteins can be expressed using cell free protein synthesis methods.

Furthermore, in some embodiments this disclosure provides a pharmaceutical preparation comprising the compositions described herein. The pharmaceutical preparation may further comprise a pharmaceutically acceptable carrier, excipient, glidant, lubricant, stabilizer, colorant, or buffer. The pharmaceutical preparation may also comprise an adjuvant. The pharmaceutical preparation may further comprise or be administered in combination with one or more conventional anti-cancer or anti-tumor agent (e.g., a chemotherapy agent), one or more conventional anti-infection agent (e.g., an antibiotic), or one or more immune-promoting agent.

The term "Single chain variable fragment (scFv)" refers to a fusion protein of the variable regions of the heavy ($V_H$) and light chains ($V_L$) of immunoglobulins, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

The term, "encoding" with respect to a specified nucleic acid, includes reference to nucleic acids which comprise the information for translation into the specified protein. The information is specified by the use of codons.

A "host cell" is a cell which can support the replication or expression of the expression vector. Host cells may be prokaryotic cells such as E. coli, or eukaryotic cells such as yeast, insect, amphibian, or mammalian cells.

As used herein, "polypeptide", "peptide" and "protein" are used interchangeably and include reference to a polymer of amino acid residues.

As used herein, "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

As used herein, "Transfection" refers to the taking up of an expression vector by a host cell, whether or not any coding sequences are in fact expressed. Numerous methods of transfection are known to the ordinarily skilled artisan.

As used herein, "Operably linked" refers to a juxtaposition of components, e.g., a regulatory region and an open reading frame, such that the normal function of the components can be performed. Thus, an open reading frame that is "operably linked" to control sequences refers to a configuration wherein die coding sequence can be expressed under the control of these sequences.

As used herein "Control Sequences" refers to nucleic acid sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize, for example, such control sequences as promoters, polyadenylation signals, and enhancers, to name but a few.

As used herein "Expression system" or "expression vector" or "vector" refers to nucleic acid sequences containing a desired coding sequence and control sequences in operable linkage, so that hosts transformed with these sequences are capable of producing the encoded proteins. To effect transformation, the expression system may be included on a vector; however, the relevant nucleic acid molecule may then also be integrated into the host chromosome.

As used herein, "cell," "cell line," and "cell culture" are used interchangeably and all such designations include progeny. Thus, "transformants" or "transformed cells" include the primary subject cell and cultures derived therefrom without regard for the number of transfers. It is also understood that all progeny may not be precisely identical in genomic content, due to deliberate or inadvertent mutations. Mutant progeny that have the same functionality as screened for in the originally transformed cell are included. Where distinct designations are intended, it will be clear from the context.

Figure 4:
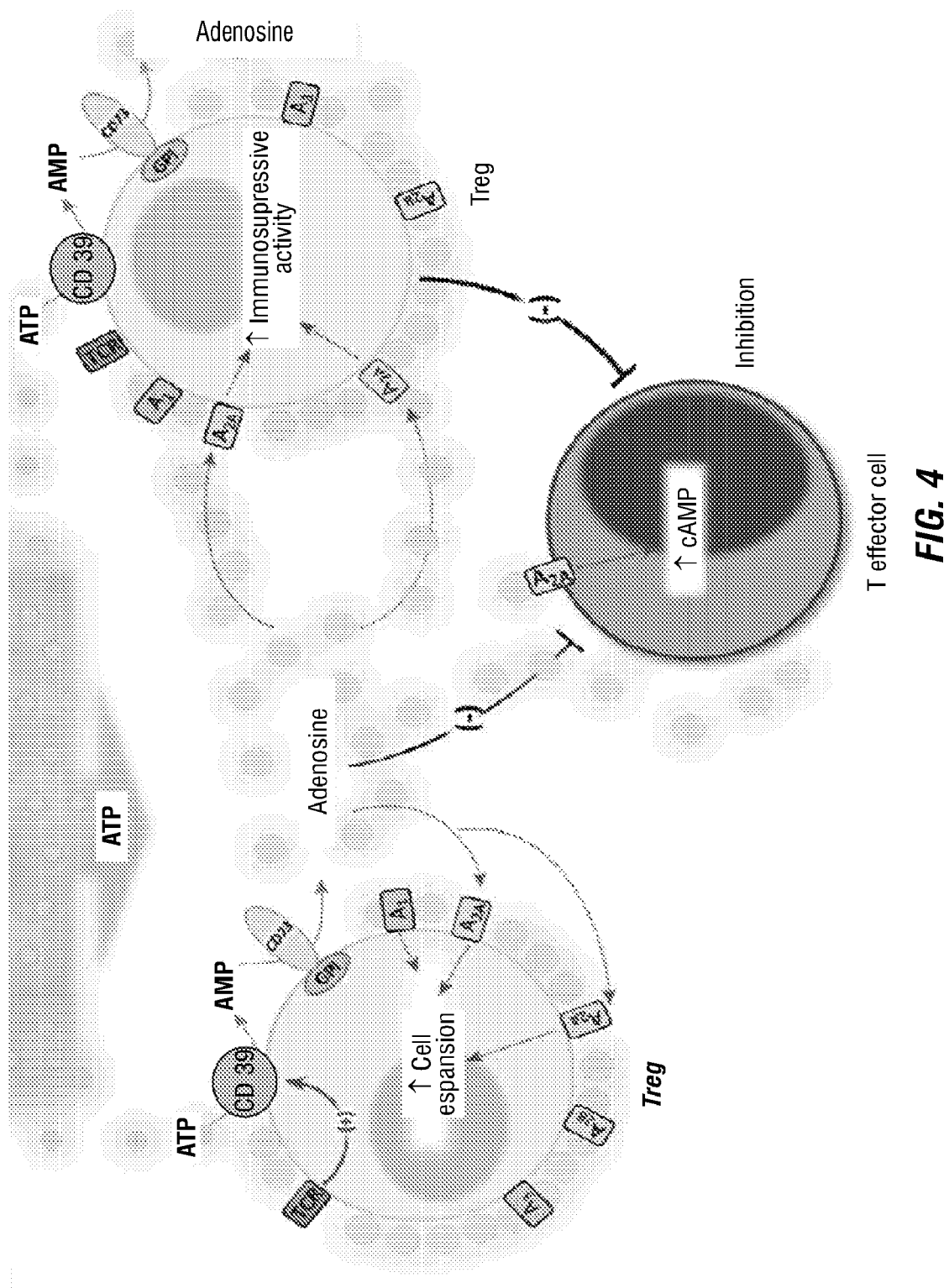
FIG. 4 is an illustration showing adenosine signaling through the immunosuppressive adenosine receptors A2AR and/or A2BR. Burnstock, G. and J.-M. Boeynaems, *Purinergic signalling and immune cells*. Purinergic Signalling, 2014. 10(4): p. 529-564 (reproduced without modification).
Figure 5:
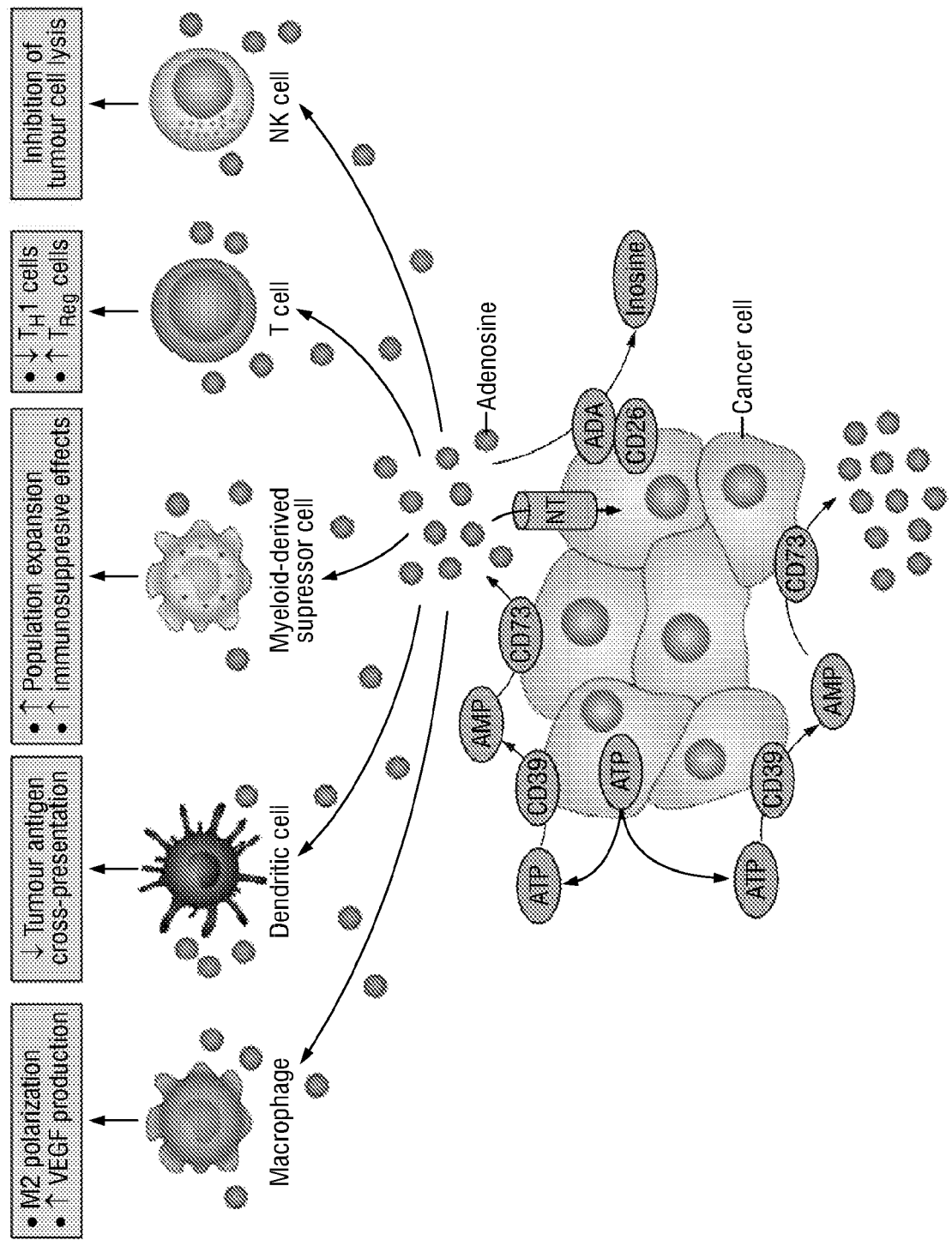
FIG. 5 is an illustration depicting the role of the adenosine pathway in the creation of an immune-tolerant tumor microenvironment. Abbreviations used (ADA (adenosine deaminase); JNK (JUN amino-terminal kinase); TH1 (T helper 1); TReg (regulatory T); VEGF (vascular endothelial growth factor)). Antonioli, L., et al., *Immunity, inflammation and cancer: a leading role for adenosine*. Nat Rev Cancer, 2013. 13(12): p. 842-857 (reproduced without modification).
Figure 6:
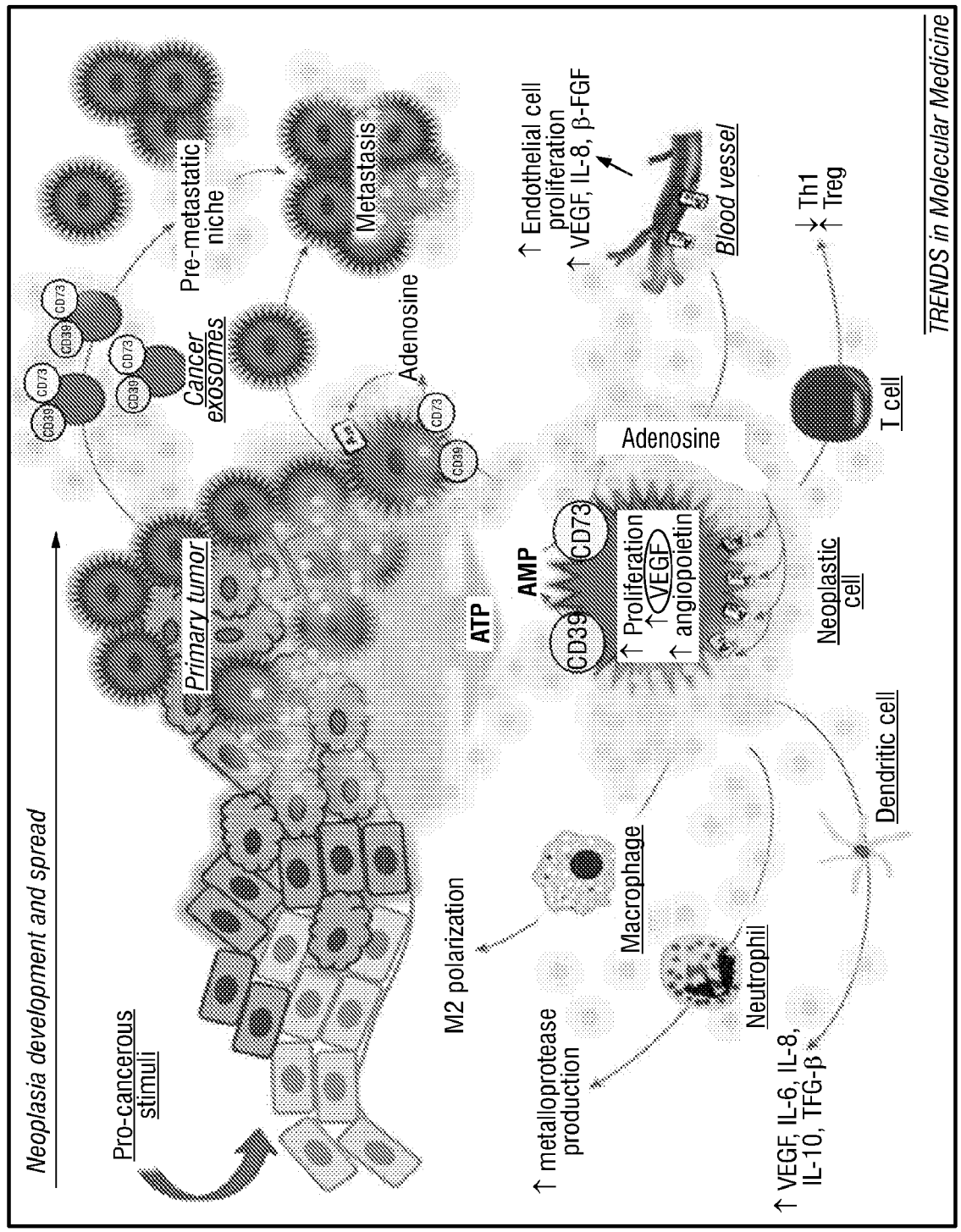
FIG. 6 is an illustration depicting the role of CD39/CD73 axis in neoplastic development and progression. Antonioli, L., et al., *CD39 and CD73 in immunity and inflammation*. Trends in Molecular Medicine, 2013. 19(6): p. 355-367 (reproduced without modification).

Extracellular adenosine (Ado) is postulated to be the principal soluble mediator of the hypoxic response within the tumor microenvironment (TME) (FIG. 1) and is by itself a marker of inflammation since under normal physiological conditions it is present at very low concentrations within the tissue microenvironment. Ado mediates signaling by binding to the adenosine family of G-protein coupled receptors (GPCRs). Ado is involved in numerous hallmarks of cancer including: (1) sustaining proliferative signaling and resisting cell death, (2) activating invasion and metastasis, and (3) inducing angiogenesis. Independent of its' oncogenic ability, Ado plays a pivotal role in creating an immunosuppressive tumor microenvironment (FIG. 4). For example, incubating Natural killer (NK) cells and cytotoxic T cells with physio-relevant concentrations of Ado (~10 µM) results in failure of these cells to efficiently kill tumor cells or secrete pro-inflammatory cytokines. Moreover, Ado stimulation of macrophages stimulates secretion of anti-inflammatory cytokines including interleukin-10 (IL-10), and inhibits secretion of pro-inflammatory cytokines like IL-1.

Figure 3:
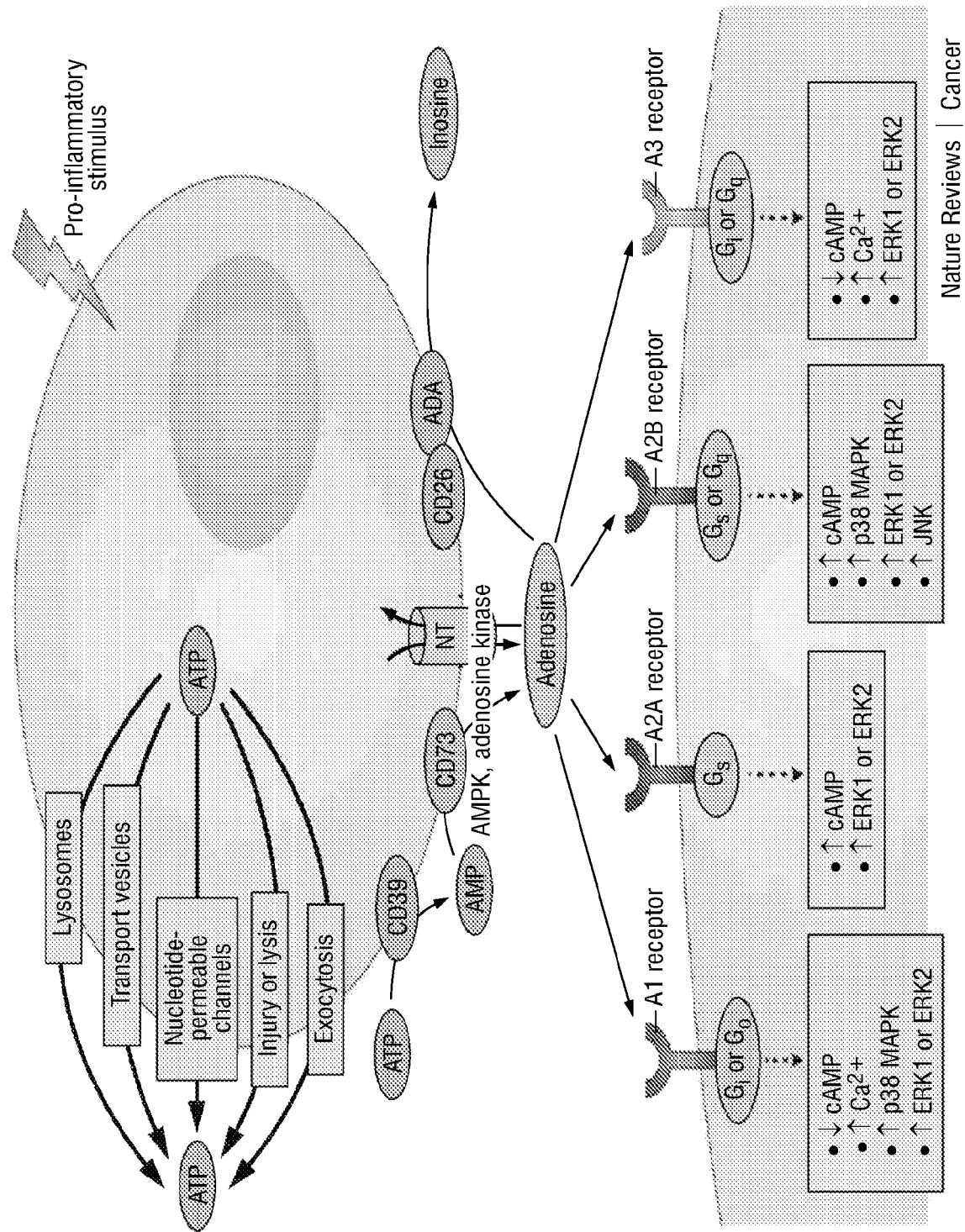
FIG. 3 is a schematic diagram illustrating the physiology of adenosine signaling, biosynthesis, catabolism of adenosine, and the second messenger pathways that are coupled to adenosine receptor subtypes. Antonioli, L., et al., *Immunity, inflammation and cancer: a leading role for adenosine*. Nat Rev Cancer, 2013. 13(12): p. 842-857 (reproduced without modification).

The physiology of adenosine signaling is depicted in FIG. 3. The occurrence of pathological events (for example, inflammation) promotes an extracellular accumulation of ATP, which is followed by its sequential degradation to AMP by the cell surface enzyme CD39 and to adenosine by CD73. Extracellular adenosine can bind to four different G-protein-coupled receptors that either stimulate (A2A and A2B) or inhibit (A1 and A3) adenylyl cyclase activity. The stimulation of A1 and A3 receptors can also stimulate the release of calcium ions from intracellular stores. Moreover, all adenosine receptors couple to mitogen-activated protein kinase (MAPK) pathways, including extracellular signal-regulated kinase 1 (ERK1), ERK2 and p38 MAPK. In the extracellular space, adenosine concentrations are controlled by adenosine deaminase (ADA; which catalyzes the conversion of adenosine into inosine) and by the activity of nucleoside transporters (NTs). cAMP, cyclic AMP; JNK, JUN N-terminal kinase.

Hence, Ado plays many different roles in promoting tumor growth and metastasis, and in enabling immunosuppression. The adenosine pathway participates in the creation of an immune-tolerant tumor microenvironment by regulating the functions of immune and inflammatory cells, such as macrophages, dendritic cells, myeloid-derived suppressor cells, T cells and natural killer (NK) cells. The adenosine pathway also regulates cancer growth and dissemination by interfering with cancer cell proliferation, apoptosis and angiogenesis via adenosine receptors that are expressed on cancer cells and endothelial cells, respectively. Solid tumors express high levels of CD39 and CD73, as well as low levels of nucleoside transporters (NTs), ecto-adenosine deaminase and its cofactor CD26, which lead to an increase in adenosine signaling in the cancer environment.

Figure 7:
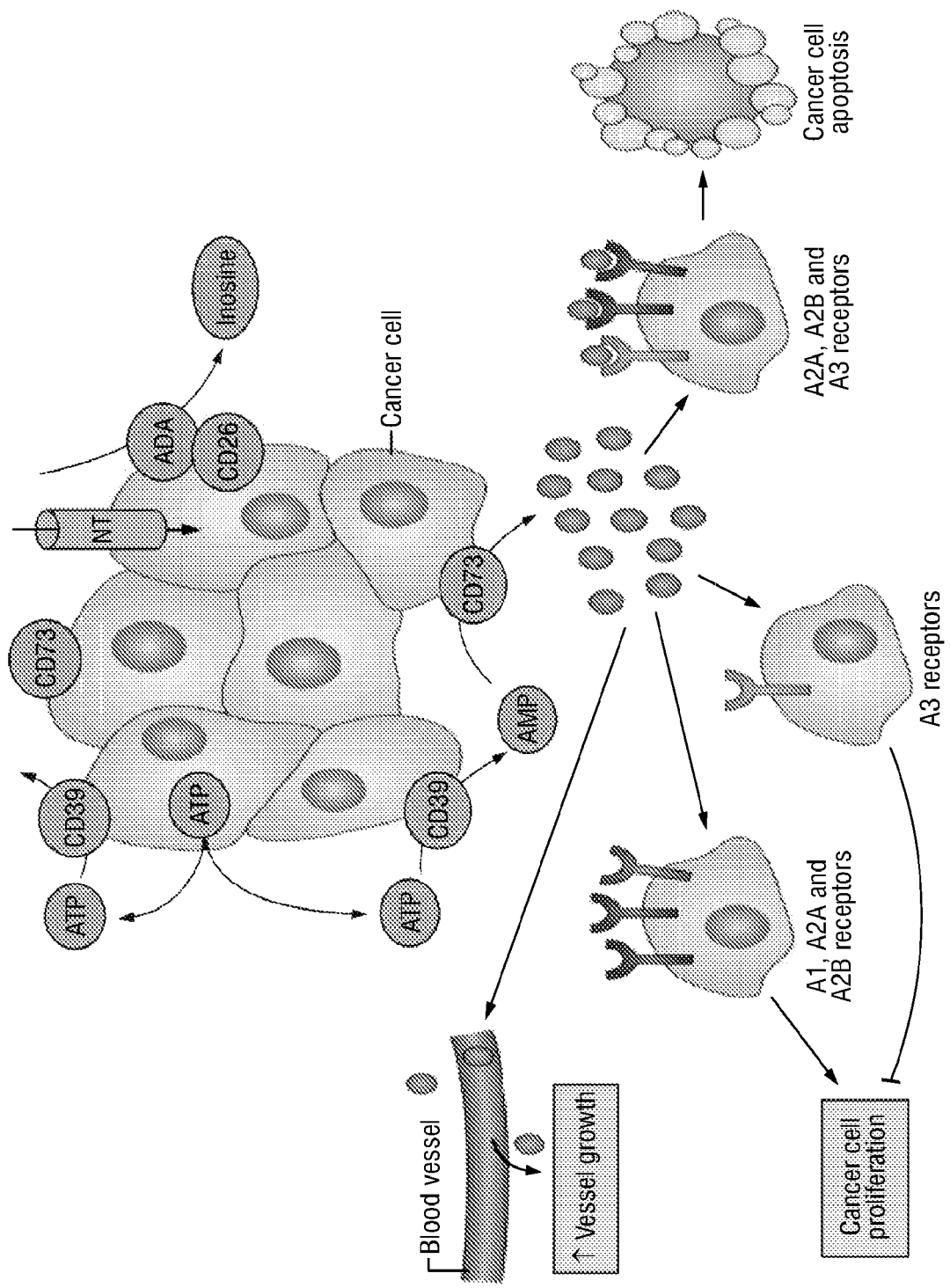
FIG. 7 is an illustration showing role of adenosine in promoting apoptosis. Antonioli, L., et al., *Immunity, inflammation and cancer: a leading role for adenosine*. Nat Rev Cancer, 2013. 13(12): p. 842-857 (reproduced without modification).
Figure 8:
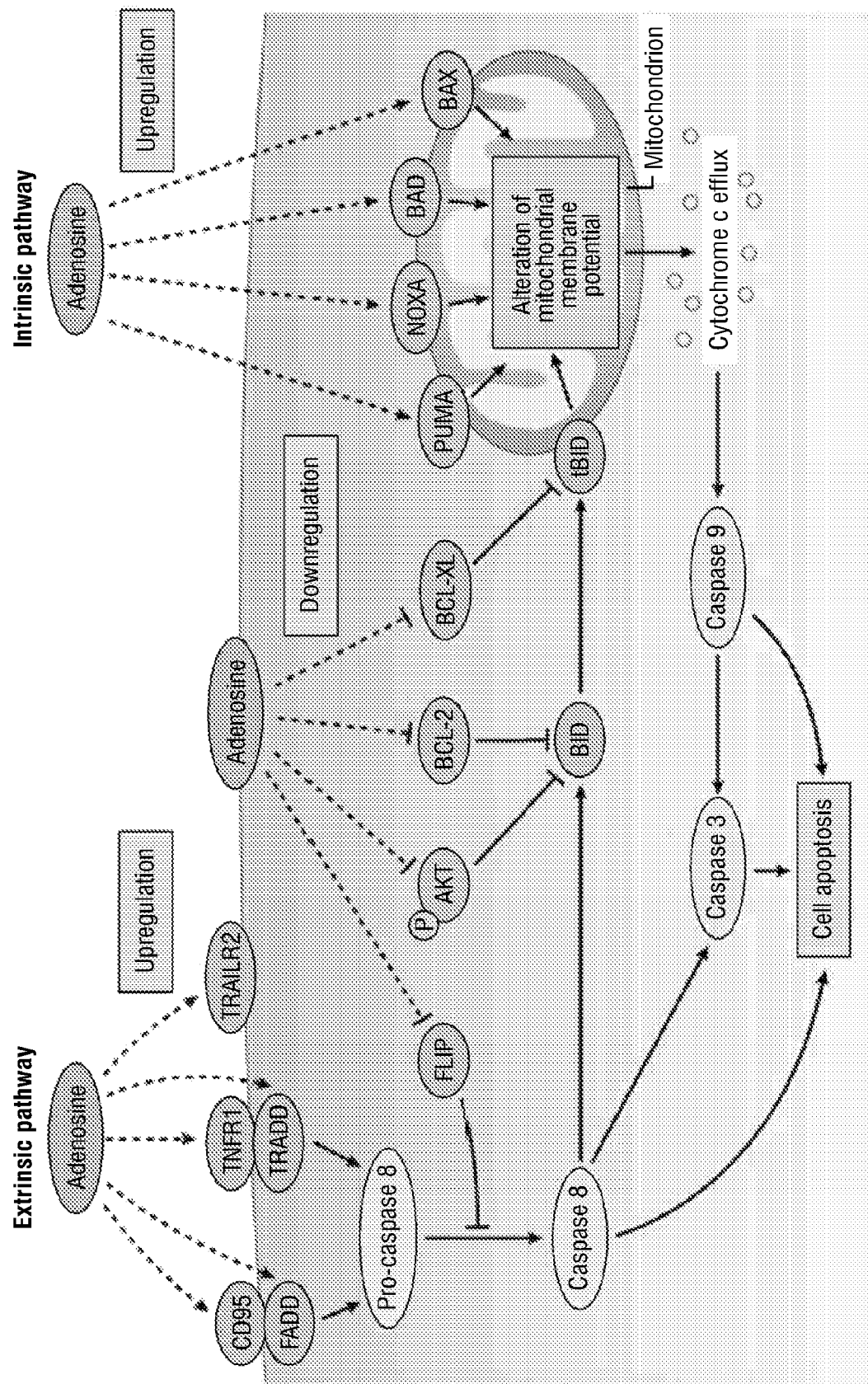
FIG. 8 shows the role of the adenosine system in modulating the extrinsic and intrinsic apoptotic programmed cell death. Antonioli, L., et al., *Immunity, inflammation and cancer: a leading role for adenosine*. Nat Rev Cancer, 2013. 13(12): p. 842-857 (reproduced without modification).

Ado plays a key role in modulating programmed cell death by controlling both, the extrinsic and intrinsic apoptotic pathways (FIG. 7 and FIG. 8). In the extrinsic pathways, adenosine upregulates the expression of death receptors—CD95, tumor necrosis factor receptor 1 (TNFR1), tumor necrosis factor-related apoptosis-inducing ligand receptor 2 (TRAILR2), as well as their downstream intracellular signaling proteins FAS-associated death domain protein (FADD) and TNFR1-associated death domain protein (TRADD). Adenosine also reduces the expression of the anti-apoptotic proteins BCL-2, FLICE-inhibitory protein (FLIP) and phosphorylated AKT. In the intrinsic pathway, adenosine upregulates the levels of several modulators of apoptosis, such as BAX, BAD, p53-upregulated modulator of apoptosis (PUMA) and NOXA. This upregulation promotes the alteration of the mitochondrial membrane potential, which is followed by an increased efflux of cytochrome c and a consequent activation of the caspase 9 cascade (FIG. 8).

Triple negative breast cancer cells (TNBCs) express high levels of the Ado receptors including A2B. Previously, it has been demonstrated in xenograft models that the aggressiveness and metastatic potential of triple negative breast cancer cells (TNBCs), like MDA-MB-231 can be drastically reduced by either antagonists or RNAi-mediated knockdown of the Ado receptor (A2B receptor). Similarly, the knockdown of A2A receptor using RNAi inhibited metastases, genetic deletion, and the antagonists of A2AR/A2BR enhanced the destruction of established tumors in mouse models of diverse tumors. In some embodiments, the ADA enzyme activates pro-inflammatory responses acting on T cells, NK cells and other innate immune cells (DCs, macrophages). Inhibiting the generation of Ado from ATP by blocking upstream pathways although shows clinical promise for the treatment of solid tumors, but does not alter the Ado concentrations already present within the tumor mass. Furthermore, Ado receptor knock out mouse strains show a delayed tumor progression and metastasis. Finally, the functional activation independent of catalytic activity provides an independent mechanism of immune-activation.

Consistent with an important role for Ado in maintaining an immunosuppressive tumor microenvironment (TME), regulatory T cells ($T_{reg}$) and myeloid derived suppressor cells (MDSC) have enhanced expression of ecto-ATPases, enzymes that facilitate the breakdown of ATP into Ado. Recent pre-clinical data has also highlighted that Ado may also limit the efficacy of anti-CTLA4 immunotherapy in metastatic melanoma. Due to the divergent expression patterns of the four Ado receptors (A1, A2A, A2B and A3), and their confounding effects on promoting tumor growth or suppression, the application of receptor agonists has been fairly limited because of the profound bystander effect.

Figure 2A:
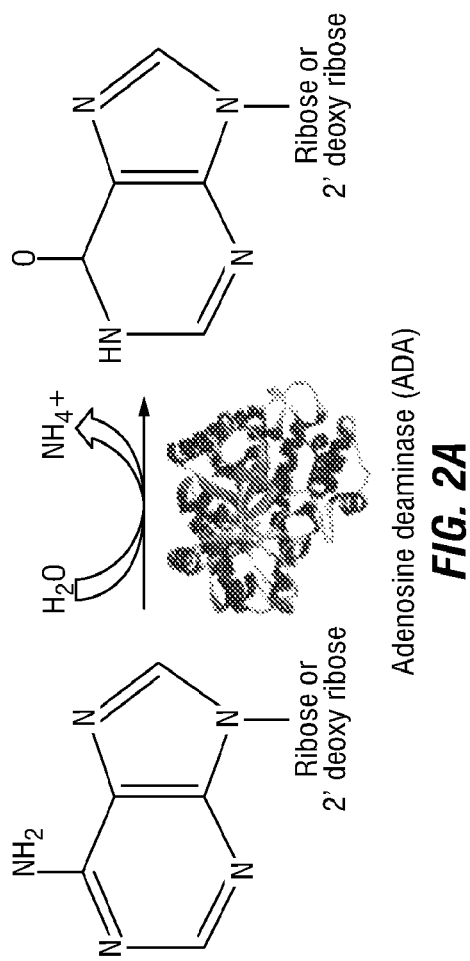
FIGS. 2A-2B show the two different anti-tumor mechanisms of Adenosine deaminase (ADA). ADA can enzymatically degrade adenosine to inosine, thus directly reversing the pro-tumor and anti-inflammatory effect of adenosine within the TME (FIG. 2A). Independent of its catalytic activity, ADA can also promote both, T-cell activation by binding to CD26, and secretion of IL-12 by dendritic cells by binding to adenosine receptor A2A (FIG. 2B).
Figure 2B:
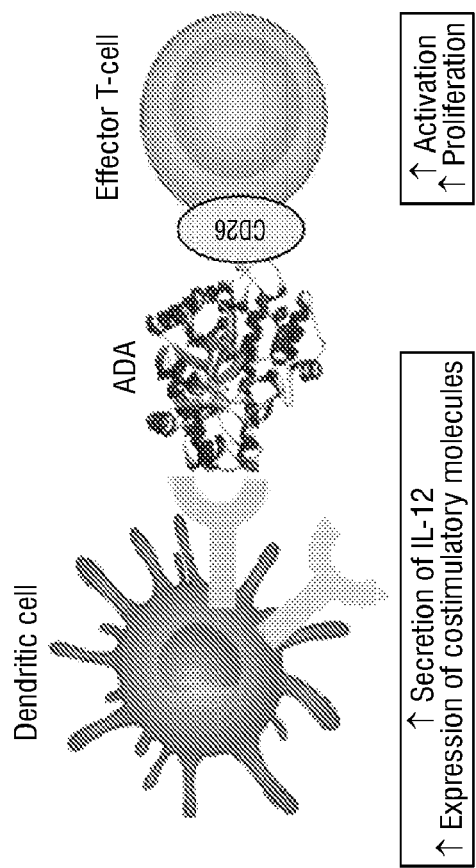
Figure 9:
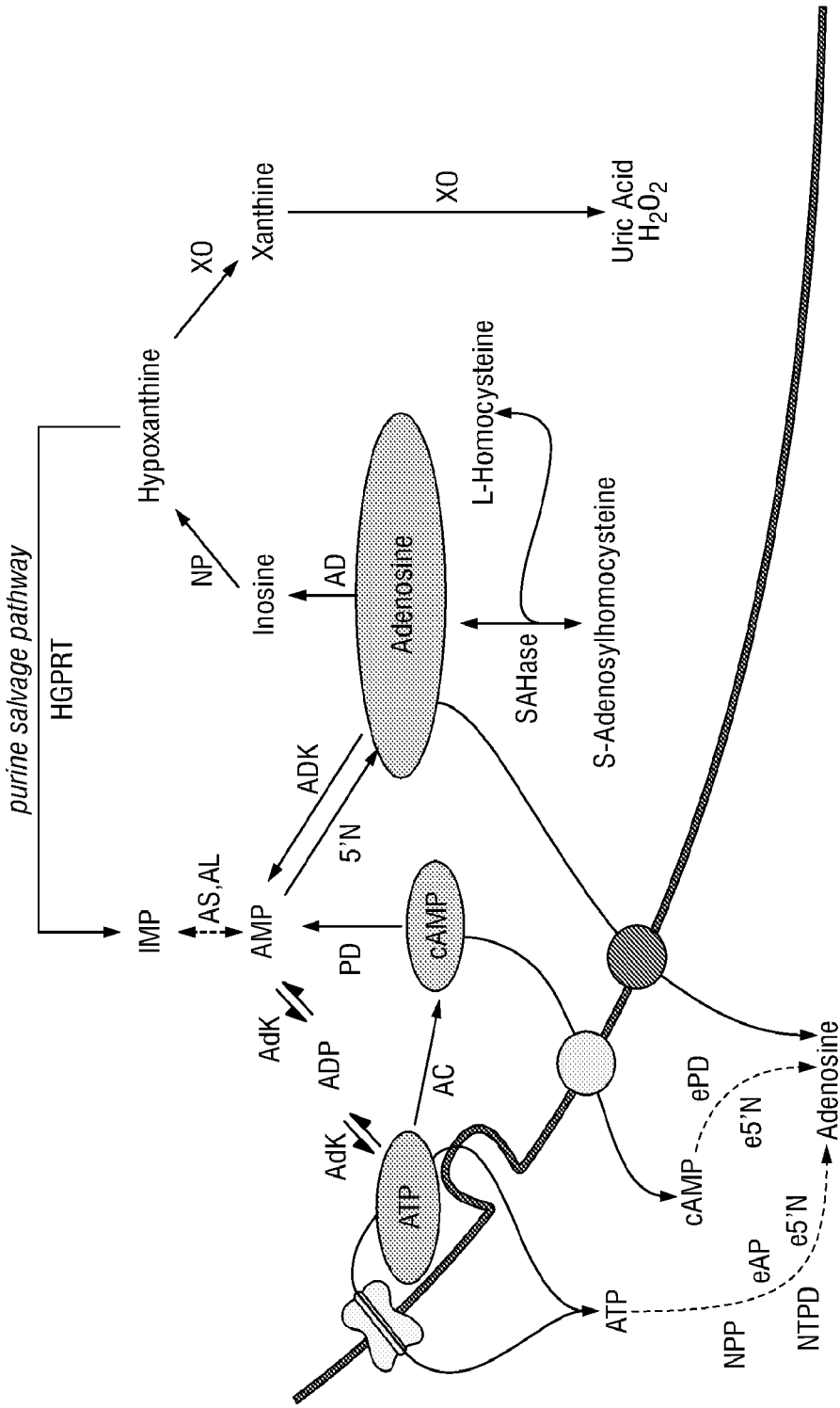
FIG. 9 shows the Adenosine Deaminase (ADA) enzymatic pathway. ADA irreversibly deaminates adenosine, converting it to the related nucleoside inosine by the substitution of the amino group for a hydroxyl group. Dale, N. and B. G. Frenguelli, *Release of Adenosine and ATP During Ischemia and Epilepsy*. Current Neuropharmacology, 2009. 7(3): p. 160-179 (reproduced without modification).

Adenosine deaminase (ADA; EC 3.5.4.4) an enzyme involved in purine metabolism, catalyzes the hydrolytic deamination of adenosine or 2'-deoxyadenosine to inosine or 2'-deoxyinosine and ammonia. For many years, ADA was considered to be cytosolic, but it has been found on the cell surface of many cell types; therefore, it can be considered an ectoenzyme. In addition, ecto-ADA has been proposed to have a catalytic-independent function as a co-stimulatory molecule in lymphocytes. Adenosine deaminase (ADA) is an enzyme responsible for the degradation of Ado into inosine and ammonia (FIG. 2 and FIG. 9). ADA is considered one of the key enzymes of purine metabolism. The high degree of amino acid sequence conservation suggests the crucial nature of ADA in the purine salvage pathway. Primarily, ADA in humans is involved in the development and maintenance of the immune system. However, ADA association has also been observed with epithelial cell differentiation, neurotransmission, and gestation maintenance. Congenital defect of ADA causes severe combined immunodeficiency, which is characterized by the absence of functional T and B lymphocytes in affected individuals. Deficient levels of ADA have also been associated with pulmonary inflammation, thymic cell death, and defective T-cell receptor signaling. Conversely, mutations causing this enzyme to be overexpressed are one cause of hemolytic anemia. There is some evidence that a different allele (ADA2) may lead to autism. Elevated levels of ADA have also been associated with AIDS. So far, two types of surface anchoring proteins for ecto-ADA have been described. The first type, with only one member, is CD26, a multifunctional protein of 110 KDa strongly expressed on epithelial cells (kidney proximal tubules, intestine, and bile duct) and on several types of endothelial cells and fibroblasts and on leukocyte subsets. The second type of ecto-ADA-binding proteins includes the adenosine receptors (AR) $A_1$ ($A_1R$) and $A_{2B}$ ($A_{2B}R$).

ADA may facilitate tumor regression by at least two independent mechanisms. ADA via its enzymatic or catalytic activity depletes Ado by converting it to inosine. Ado is involved in stimulating tumor growth and promotes immune suppression. In some embodiments the ADA enzyme catalytically degrades Ado to generate inosine (not immunosuppressive at physio-relevant concentrations) and ammonia. Depletion of Ado is postulated to have both a direct effect on tumor cells and on relieving suppression on immune cells (FIG. 10). Independent of its catalytic activity, ADA via its binding to its specific surface anchoring proteins may activate an anti-tumor immune response. For example, ADA binds to CD26 on T cells to promote activation and proliferation of T cells.

Success of chemotherapy has been attributed to their ability to induce immunogenic cell death. Release of ATP from dying cells is considered one of the alarm signals of effective chemotherapeutic agents including oxyplatin and anthracyclines. As outlined in FIG. 1, this ATP is readily converted to Ado due to CD39/CD73 overexpression within the TME. Since it has been demonstrated that inhibiting Ado production can partially reverse resistance to doxorubicin chemotherapy, and can enhance survival and promote tumor regression, it is likely that combining chemotherapy with ADA provide synergistic effects.

The immunosuppressive TME that promotes peripheral tolerance of tumor-directed immune responses is considered as the primary factor for the failure of antibody therapy (e.g. Herceptin) and immunotherapies. Inhibition of specific Ado receptors through small molecule antagonists has shown to improve the efficacy of both antibody mediated immunotherapy and adoptive cell therapy in mouse models.

For example, inhibitory receptors such as anti-cytotoxic T-lymphocyte antigen 4 (CTLA-4) and programmed death 1 (PD-1), expressed on tumor-specific T cells lead to compromised activation and suppressed effector functions such as proliferation, cytokine secretion, and tumor cell lysis. Modulating these receptors using monoclonal antibodies, an approach termed "immune checkpoint blockade," has gained momentum as a new approach in cancer immunotherapy. Antibodies directed against PD-1 and its ligand, PD-L1, have shown much promise in the treatment of melanoma, renal cell cancer, non-small cell lung cancer, and other tumors, as evident by encouraging rates and durability of tumor responses. The present disclosure contemplates an adenosine deaminase (ADA) fusion protein expressed as ADA fused to the single chain variable fragment (scFv) and able to target targeting PD-1/CTLA-4. These "dual-hit" immunoenzymes will home to the tumor and provide concomitant blockade of two separate immuno-checkpoints (inhibitory receptor and Ado).

In some embodiments, the present disclosure pertains to a method of treating a solid tumor. Such a method comprises detecting expression of at least one adenosine-dependent pathway protein in a subject in need thereof. In some embodiments, the method comprises administering to the subject a therapeutically effective amount of a composition comprising adenosine deaminase. In some embodiments, the composition comprises a polynucleotide encoding an adenosine deaminase fusion protein. In some embodiments, the polynucleotide encoding the fusion protein comprises a first polynucleotide that encodes a targeting molecule. In some embodiments, the polynucleotide encoding the fusion protein comprises a second polynucleotide that encodes adenosine deaminase. In some embodiments, the targeting molecule encoded by the first polynucleotide is specific for a tumor associated antigen expressed in the tumor microenvironment of the solid tumor. In some embodiment, the method is effective in inhibiting tumor growth, metastasis, and angiogenesis.

In some embodiments, the present disclosure pertains to a method of activating an anti-tumor immune response for the treatment of a cancer. In some embodiments, such a method comprises detecting expression of at least one adenosine deaminase binding protein in a subject in need thereof. In some embodiments, the method comprises administering to the subject a therapeutically effective amount of a composition comprising adenosine deaminase. In some embodiments, the adenosine deaminase binding protein is selected from a group consisting of CD26, A (1) adenosine receptors, A (2A) adenosine receptors, A (2B) adenosine receptors, and A3 adenosine receptors and a combination thereof. In some embodiments, the subject has a cancer comprising of a solid tumor. In some embodiments, the subject has a cancer comprising of leukemia. In some embodiments, the administration of adenosine deaminase to the subject stimulates an anti-tumor immune response. In some embodiments, the anti-tumor immune response comprises of T cell proliferation and activation of maturation of macrophages or dendritic cells.

In some embodiments, the present disclosure pertains to a method for targeted reduction of adenosine or deoxyadenosine in a tumor microenvironment of a solid tumor. In some embodiments, such a method comprises detecting expression of at least one adenosine deaminase binding protein in a subject in need thereof. In some embodiments, the method comprises administering to the subject a therapeutically effective amount of a composition comprising adenosine deaminase. In some embodiments, the adenosine deaminase binding protein is selected from a group consisting of CD26, A (1) adenosine receptors, A (2A) adenosine receptors, A (2B) adenosine receptors, and A3 adenosine receptors and a combination thereof. In some embodiments, the method comprises administering to the subject an effective amount of a composition comprising polynucleotide encoding an adenosine deaminase fusion protein. In some embodiments, the targeted reduction of adenosine within the tumor microenvironment inhibits tumor growth, metastasis, and angiogenesis.

In some embodiments, the present disclosure pertains to a method of treating a solid tumor. In some embodiments, such a method comprises detecting expression of at least one adenosine deaminase binding protein in a subject in need thereof. In some embodiments, the method comprises administering to the subject a therapeutically effective amount of a composition comprising adenosine deaminase. In some embodiments, the adenosine deaminase binding protein is selected from a group consisting of CD26, A (1) adenosine receptors, A (2A) adenosine receptors, A (2B) adenosine receptors, and A3 adenosine receptors and a combination thereof. In some embodiments, the composition comprises a polynucleotide encoding an adenosine deaminase fusion protein. In some embodiments, the polynucleotide encoding the fusion protein comprises a first polynucleotide that encodes a targeting molecule a second polynucleotide that encodes adenosine deaminase. In some embodiments, the targeting molecule encoded by the first polynucleotide is specific for a tumor associated antigen expressed in the tumor microenvironment of the solid tumor.

In some embodiments, the present disclosure relates to a method of altering the tumor microenvironment in a subject in need thereof. In some embodiments, the subject suffers from a solid tumor. In some embodiments, such a method comprises detecting expression of at least one adenosine deaminase binding protein in a subject in need thereof. In some embodiments, the method comprises administering to the subject a therapeutically effective amount of a composition comprising adenosine deaminase. In some embodiments, the adenosine deaminase binding protein is selected from a group consisting of CD26, A (1) adenosine receptors, A (2A) adenosine receptors, A (2B) adenosine receptors, and A3 adenosine receptors and a combination thereof. In some embodiments, the ADA comprises a recombinant adenosine deaminase. In some embodiments, the recombinant adenosine deaminase is conjugated to polyethylene glycol. In some embodiments, the polyethylene glycol ranges in size from about 4,000 to about 45,000 Daltons.

In some embodiments, the composition comprises a polynucleotide encoding an adenosine deaminase fusion protein. In some embodiments, the polynucleotide encoding the fusion protein comprises a first polynucleotide that encodes the targeting molecule; and a second polynucleotide that encodes adenosine deaminase. In some embodiments, the targeting molecule encoded by the first polynucleotide is specific for a tumor associated antigen expressed in the tumor microenvironment of the solid tumor.

In some embodiments, the subject is undergoing antibody mediated immunotherapy. In some embodiments, the administration of adenosine deaminase causes an enhanced sensitivity to antibody mediated immunotherapy. In some embodiments, the composition further comprises a pharmaceutically acceptable excipient or an adjuvant. In some embodiments, the adenosine deaminase is the ADA (isoenzyme 1).

In some embodiments, the present disclosure pertains to a method of overcoming resistance of a tumor to a chemotherapeutic agent in a subject in need thereof. In some embodiments, such a method comprises detecting expression of at least one adenosine deaminase binding protein in a subject in need thereof. In some embodiments, the method comprises administering to the subject a therapeutically effective amount of a composition comprising adenosine deaminase. In some embodiments, the adenosine deaminase binding protein is selected from a group consisting of CD26, A (1) adenosine receptors, A (2A) adenosine receptors, A (2B) adenosine receptors, and A3 adenosine receptors and a combination thereof.

In some embodiments, the present disclosure relates to a method of improving the efficacy of antibody mediated immunotherapy of a tumor. In some embodiments, such a method comprises detecting expression of at least one adenosine deaminase binding protein in a subject in need thereof. In some embodiments, the method comprises administering to the subject a therapeutically effective amount of a composition comprising adenosine deaminase. In some embodiments, the adenosine deaminase binding protein is selected from a group consisting of CD26, A (1) adenosine receptors, A (2A) adenosine receptors, A (2B) adenosine receptors, and A3 adenosine receptors and a combination thereof. In some embodiments, the subject is undergoing antibody therapy for a solid tumor.

The methods of the present disclosure may use various compositions comprising adenosine deaminase. In an exemplary embodiment, the methods and treatments of the present disclosure may utilize a purified human adenosine deaminase (EC 3.5.4.4). In some embodiments, the adenosine deaminase is adenosine deaminase CECR1 (also known as ADA2). In some embodiments, the adenosine deaminase is a recombinant adenosine deaminase. In some embodiments, the adenosine deaminase (ADA) is engineered to remove cysteines. In some embodiments, the ADA is engineered to mutate two cysteine residues to two serine residues, while keeping the disulfide bond intact. In some embodiments of the present disclosure, the recombinant adenosine deaminase is expressed fused to the Fc portion of an immunoglobulin. In some embodiments, the Fc portion of the immunoglobulin is mutated to reduce or inhibit antibody dependent cell-mediated cytotoxicity (ADCC) or complement dependent cytotoxicity (CDC). In some embodiments, the immunoglobulin is IgG1 or IgG4 subtypes.

In some embodiments, the methods and treatments of the present disclosure utilize a composition comprising an adenosine deaminize fusion protein. In some embodiments, such a composition comprises a polynucleotide encoding an adenosine deaminize fusion protein. In some embodiments, the polynucleotide encoding the fusion protein comprises a first polynucleotide that encodes a targeting molecule and a second polynucleotide that encodes adenosine deaminize. In some embodiments the targeting molecule encoded by the first polynucleotide is specific for a tumor associated antigen expressed in the tumor microenvironment of the solid tumor. In some embodiments, the first polynucleotide and the second polynucleotide are operably linked via a third polynucleotide. In some embodiments, the third polynucleotide encodes a polypeptide linker between the targeting molecule and the adenosine deaminize. In some embodiments, the polypeptide linker is a $(Gly_4Ser)_3$ peptide. Within certain embodiments, the polynucleotide encoding the ADA fusion protein is a component of a vector, such as a plasmid vector or a viral vector. Within certain embodiments, the polynucleotide encoding the ADA fusion protein is a component of a vector, such as a plasmid vector or a viral vector, where the vector comprises a transcriptional promoter operably linked to the first polynucleotide.

In some embodiments of the present disclosure, the tumor associated antigen encoded by the first polynucleotide is selected from a group consisting of products of mutated oncogenes, products of tumor suppressor genes, products of mutated genes, overexpressed and/or aberrantly expressed cellular proteins, tumor antigens produced by oncogenic viruses, altered cell surface glycolipids and/or glycoproteins, and cell type-specific differentiation antigens. In some embodiments, the tumor associated antigen is Her2/neu. In some embodiments, the tumor associated antigen is selected from the group consisting of PD1, TIM-3, LAG-3, and CTLA4.

In some embodiments, the present disclosure relates to a composition comprising an adenosine deaminase fusion protein. In some embodiments, the adenosine deaminase fusion protein comprises a polynucleotide for expressing a scFv/adenosine deaminase (ADA) fusion protein. In some embodiments, the polynucleotide that encodes a scFv/ADA fusion protein comprises a first polynucleotide that encodes a scFv and a second polynucleotide that encodes ADA. In some embodiments, the first polynucleotide and the second polynucleotide are operably linked such that together they encode a fusion protein comprising a scFv and an ADA. In some embodiments, the first polynucleotide and the second polynucleotide are operably linked by a third polynucleotide that encodes a polypeptide linker between the scFv and the ADA. Within certain embodiments, the polynucleotide encoding the scFv/ADA fusion protein is a component of a vector, such as a plasmid vector or a viral vector, wherein the vector comprises a transcriptional promoter operably linked to the scFv encoding polynucleotide. In an exemplary embodiment, the first polynucleotide may target a tumor associated antigen. In some embodiments, the tumor associated antigen may be Her2, CD20 or immune checkpoint molecules like PD-L1 or PD-1.

In some embodiments, the methods and treatments of the present disclosure comprise the detecting adenosine deaminase binding protein in a subject in need thereof. In some embodiments, the adenosine deaminase binding protein is selected from a group consisting of CD26, A (1) adenosine receptors, A (2A) adenosine receptors, A (2B) adenosine receptors, and A3 adenosine receptors and a combination thereof. In some embodiments, the adenosine deaminase proteins are detected within a tumor microenvironment, or on peripheral blood tumor cells, or T cells of the subject. In various embodiments of the present disclosure, the adenosine deaminase binding proteins are detected using standard and known methodologies. In exemplary embodiments, adenosine deaminase binding proteins are detected using flow cytometry, immunohistochemistry on formalin fixed paraffin embedded tissue biopsy, PCR, quantitative PCR or sequencing.

The compositions disclosed herein may be administered to a subject in need by a variety of conventional routes of administration, including orally, topically, parenteral, e.g., intravenously, or subcutaneously. Further, the compositions may be administered intranasal, as or a rectal suppository, or using a "flash" formulation. Furthermore, the compositions may be administered to a subject in need of treatment by controlled release dosage forms, site specific drug delivery, by stereotactic injection, liposomes, or in nanoparticles. In some embodiments, the adenosine deaminase is conjugated to polyethylene glycol. In some embodiments, the polyethylene glycol ranges in size from about 4,000 Daltons to about 45,000 Daltons. In some embodiments of the present disclosure, the adenosine deaminase is administered using nanoparticles, bacteria, or oncolytic viruses.

When administering the complexes of the present disclosure parenterally, the complexes may generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Non-aqueous vehicles such a cottonseed oil, sesame oil, olive oil, soybean oil, corn oil, sunflower oil, or peanut oil and esters, such as isopropyl myristate, may also be used as solvent systems for the compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present disclosure, however, any vehicle, diluent, or additive used would have to be compatible with the complexes.

Sterile injectable solutions can be prepared by incorporating the complexes utilized in practicing the present invention in the required amount of the appropriate solvent with various other ingredients, as desired.

A pharmacological formulation of the present invention can be administered to the patient in an injectable formulation containing any compatible carrier, such as various vehicle, adjuvants, additives, and diluents; or the complexes utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Many other such implants, delivery systems, and modules are well known to those skilled in the art.

In some embodiments, the methods and treatment disclosed herein may be combined with other therapeutic modalities. For example, the methods and treatments of the present disclosure may be combined with adoptive cell therapy including chimeric antigen receptor T cells, tumor infiltrating lymphocytes, or expanded NK cells. In some embodiments, the methods and treatments disclosed herein are combined with tumor vaccination. In some embodiments, ADA therapeutic treatment is provided in an adjuvant or neo-adjuvant setting. In some embodiments of the present disclosure ADA may be administered in combination with administration of at least one other anti-tumor agent. In some embodiments, the anti-tumor agent is selected from a group consisting of chemotherapeutic agents, radiotherapeutic agent, cytokines, anti-angiogenic agents, apoptosis-inducing agents, and anti-cancer immunotoxins.

Application and Advantages

Employing ADA as a therapeutic to deplete Ado within the tumor microenvironment (TME) represents an advantageous mechanism of immunotherapy that acts by destroying a pro-tumor (and pro-metastatic) and anti-inflammatory small molecule. This is in contrast to immunomodulatory antibodies that simply function by binding/blocking (and/or cell-depletion). Secondly, the enzymatic depletion also overcomes concerns associated with targeting through pharmacological receptor antagonists that present both efficacy and off-target safety concerns, and only offer partial shutdown of Ado receptor derived signaling. Unlike antibodies and other affinity reagents that are stoichiometric, enzymes are catalytic and can facilitate conversion of multiple Ado molecules and therefore require lower dosing. One of the great barriers of cancer treatments is the ability of tumor cells to quickly establish resistance. Unlike chemotherapy or antibody directed therapy or even pharmacological inhibitors, Ado depletion via ADA provides no obvious pathway to select for resistant cells. This is because of the well-documented link between hypoxia and Ado. Despite this, if the tumor cells inhibit the production of the Ado as a resistance mechanism, it is likely to reduce Ado derived immunosuppression (FIG. 1).

Moreover, ADA can bind to the T-cell activation molecule CD26 with nanomolar affinity. This binding of ADA (human and bovine but not the mouse ADA) to CD26 is independent of its catalytic activity. Cross-linking of CD26 has been shown to promote T-cell proliferation and polarization towards a Th1/Tc1 type (pro-inflammatory and anti-tumor). Similarly, ADA can bind to the Ado receptors (A2A/A2B) on cells of the monocytic lineage (macrophages/dendritic cells) and promote their pro-inflammatory maturation. Furthermore, PEGylated-bovine ADA has been approved by the FDA for the treatment of individuals with genetic deficiencies in ADA that result in Severe Combined Immunodeficiency (SCID), and thus there exists a direct pathway to clinical translation.

ADDITIONAL EMBODIMENTS

Reference will now be made to more specific embodiments of the present disclosure and experimental results that provide support for such embodiments. However, Applicants note that the disclosure below is for illustrative purposes and is not intended to limit the scope of the claimed subject matter in any way.

Example 1

Ado and its Analogues.

Ado or 2-chloro Ado (cADO, a more stable analogue of Ado), as appropriate may be utilized. Furthermore, both Ado receptors agonists, including 5'-(N-Ethylcarboxamido) adenosine (NECA), and antagonists including Erythro-9-(2-hydroxy-3-nonyl) adenine (EHNA), are well described.

Example 2

Molecular Engineering of hADA/mADA Constructs

Although PEGylated bADA (bovine adenosine deaminase) is FDA approved, there are two drawbacks to evaluating this as a therapeutic agent in the current context: (a) immunogenicity and (b) the ability of PEGylation to interfere with binding of ADA to Ado receptors and/or CD26 has not been well-studied. Instead, Applicants cloned the hADA (human adenosine deaminase) with a secretion leader sequence and a c-terminal hexahistidine tag, transfected HEK293 cells and selected for stable transfectants. Subsequent to protein expression and purification, the enzymatic activity was calibrated using the standard Ado spectrophotometric assay. It should be noted that intramuscular injection of the bADA has not shown any toxicity and hence the CD26/Ado receptor binding is not anticipated to lead to unexpected homing to tissues. On the contrary, tumors and the surrounding stroma have been shown to upregulate CD26 and this might serve to localize the hADA to the tumor microenvironment (TME). Second, hADA is extremely proficient catalyst (kcat/KM for Ado, $\sim 7\times10^6$ $M^{-1}$ $s^{-1}$) and has a broad pH tolerance. Hence the activity of the enzyme is not likely to be altered by the acidic TME. Third, to increase in vivo half-life of hADA, Applicants fused the C-terminus of the ADA to Fc portion of non-lytic antibodies, essentially as described previously.

Example 3

In Vitro Evaluation of the Effect of Purified ADA to Affect the Viability of Human Breast Cancer Cell Lines.

In order to examine the ability of hADA/mADA on cell viability, cell-viability time curves were generated by treating a panel of triple negative breast cancer cell lines (TNBC) including MDA-MB-231 and 4T1 cells, using the standard MTT assay, as described previously. Briefly, the cells were incubated with increasing concentrations of Ado (0-50 μM) and treated with differing concentrations of purified hADA/mADA (0-100 units of enzyme) and their viability measured.

In parallel, the frequency of apoptotic cells under these same treatment conditions was quantified by a combination of Annexin V and propidium iodide (PI) staining. The mechanistic basis of the response was tested by measuring the inosine concentrations in the supernatants on the HPLC. In order to determine if incubation with ADA causes an altered expression of the Ado receptors, mRNA was extracted from populations of tumor cells and subject to RT-PCR to quantify transcripts corresponding to the Ado receptors A1, A2A, A2B and A3. This is necessary due to the lack of well-validated antibodies directed against these receptors.

Example 4

Migration, Wound Healing and Colony Formation Assays.

Since it is well documented that Ado can promote metastasis by facilitating the migration and invasion of breast cancer cells, the ability of hADA to inhibit these functions in vitro will be studied as function of both Ado and hADA/mADA concentrations, as described above. In order to quantify invasive potential of cells, the treated cells were incubated on the upper well of a transwell plate and their ability to migrate across a Matrigel coated insert quantified. Wound healing assay mimics cell migration during wound healing in vivo. The assay procedure involves creating a wound in a cell monolayer and then monitoring the closure of wound, on account of cell migration, over different intervals of time, and will be performed essentially as described previously. The colony formation assay is a standard assay for accessing the tumorigenic potential of cancer cells, and the ability of hADA/mADA to attenuate the tumorigenic potential of breast cancer cells would be assessed using this assay. Third, the ability of hADA/mADA to reverse the increase in anchorage independent growth of breast cancer cells will be studied using the soft agar colony formation assays, essentially as described previously.

Example 5

Cell Cycle Progression and DNA Synthesis Ability

Active DNA synthesis and sustained cell cycle progression are a hallmark of cancer progression. In this context we will test the DNA synthesis ability and cell cycle progression of TNBC cells with or without Ado and/or hADA/mADA. Briefly, the cancer cells will be grown on coverslips with the addition of EdU, the nucleoside analogue of thymidine. The cells will be scored for EdU positivity cells using standard microscopy techniques. Similarly, the proliferation indices of these cells will also be measured by quantifying DNA content in single cells on the flow cytometer.

Example 6

Quantifying the Ability of hADA/mADA to Reverse Inhibition of Cytotoxicity Mediated by Human Natural Killer NK/CD8+ T Cells.

It is well documented that Ado signaling through the Ado receptors can inhibit the effector functionality of immune cells. Co-culture studies of TNBC cells and immune cells (T cells, NK cells) in presence or absence of hADA/mADA will be performed. Briefly, NK cells or T cells will be cultured with Ado (or analogues) in the with or without ADA for a period of 12-24 h, and the cytotoxic ability of these NK/CD8+ T cells will be tested using a redirected killing assay, essentially as described previously.

Example 7

Reversing Ado Mediated Inhibition of Human T-Cell/NK-Cell Cytokine Secretion and Proliferation In order to quantify the ability of hADA/mADA to reverse the inhibition of cytokine secretion mediated by Ado, NK/CD8+ T cells isolated ex vivo will be activated for a period of 3 days, and further incubated with Ado (or analogues) with or without hADA/mADA for 24 h. For CD4+ T cells, the appropriate polarizing conditions will be utilized during polarization to enable differentiation of Th1, Th2 or Th17 cells. After appropriate washing, the immune cells will be activated with αCD3/αCD28 beads and the concentrations of IL-2, IL-4, IL-10, IL-17, and TNFα will be quantified using multiplexed bead based ELISA.

Example 8

Quantifying Intracellular cAMP Concentrations in Human Immune Cells

Activation of the Ado receptors by extracellular Ado results in increased intracellular concentration of cyclic AMP (cAMP) which in turn is linked to inhibition of NK/T-cell effector functionality. Activated human NK/T cells will be incubated with Ado (or analogues) with or without ADA for 3 h in the presence of αCD3/αCD28 beads, and the intracellular cAMP concentrations in cells will be determined subsequent to lysis by utilizing the protein kinase A (PKA) assay, essentially as described previously.

Example 9

Mechanistic Insight into the Role of ADA in Immune Mediated Killing

In some embodiments, the present disclosure utilizes the dual role of ADA in combating cancer. First, by monitoring the changes in the level of extracellular Ado in presence or absence of ADA (by HPLC) in parallel with growth of cancer cells, we would be able to establish the anticancer catalytic role of ADA. Second, using western blotting (WB), RT-PCR and ELISA based assays we will evaluate the mechanistic role of ADA in combating cancer independent of its catalytic activity by pretreatment of hADA/mADA with Hg2+. Hg2+ pretreatment abolishes the catalytic ability of the enzyme to degrade Ado without altering its ability to bind either the Ado receptors or CD26. These results would primarily help us evaluate the immune activating role ADA independent of its catalytic activity. The mADA also serves as an additional control, since it is strictly a catalytic enzyme and does not bind human or mouse CD26.

hADA but not the mADA has the ability to act as a costimulatory molecule (FIG. 2) whereas Ado has the opposite immunosuppressive act. Human peripheral blood mononuclear cells (PBMC) will be incubated with beads coated with αCD3/hADA and the proliferation of T cells will be studied in the presence or absence of Ado (or analogues) using standard CFSE assays. Simultaneously, the quantity of IL-12 in the supernatants can be measured using ELISA, to quantify activation of antigen presenting cells. Parallel experiments set up with mADA will help identify the relative contributions of each function of ADA.

Example 10

Her2 positive breast cancer patients are treated with a combination of Herceptin and recombinant human ADA. Alternately, the patients are treated with a polypeptide comprising a fusion between scFv targeting Her2, human ADA and Fc region of an antibody.

Example 11

TNBC patients are treated with a combination of anthracycline (chemotherapy) and human ADA.

Example 12

Melanoma patients are treated with a polypeptide comprising a fusion between scFv targeting PD-1, human ADA and Fc region of an antibody. Alternately, the patients are treated using a mixture of the antibody against PD-1 and human ADA.

Example 13

Purification of mADA mADA-His and mADA-Fc was detected in the supernatant of HEK293F cells as shown by WB using Anti-His antibody (FIG. 10A). mADA-His was purified with Ni-NTA Column (FIG. 10B). The impurities were further removed using ion exchange chromatography (FIGS. 10C-10D). The purity of mADA-His was checked by loading the recovered elute on to a SDS PAGE and the gel was stained with coomassie blue (FIG. 10D). The binding efficiency of mADA-Fc to Anti IGg antibody for purification using sandwich ELISA was assessed (FIGS. 10E, 11A and 11B). Briefly, anti-ADA antibody was quoted on the wells of 96 well microtiterplate overnight. Blocking with 5% milk was performed at room temp. Later mADA-Fc supernatant was added to the wells followed by incubation for two hours. After washing with PBST, HRP conjugated anti-IGg antibody was used as the detection antibody. The absorbance was measured with microtiter plate reader. Anti-IGg antibody did indeed bind to mADA-Fc.

Example 14

Stability of mADA Enzymatic Activity in Cell Culture Medium

Figure 12A:
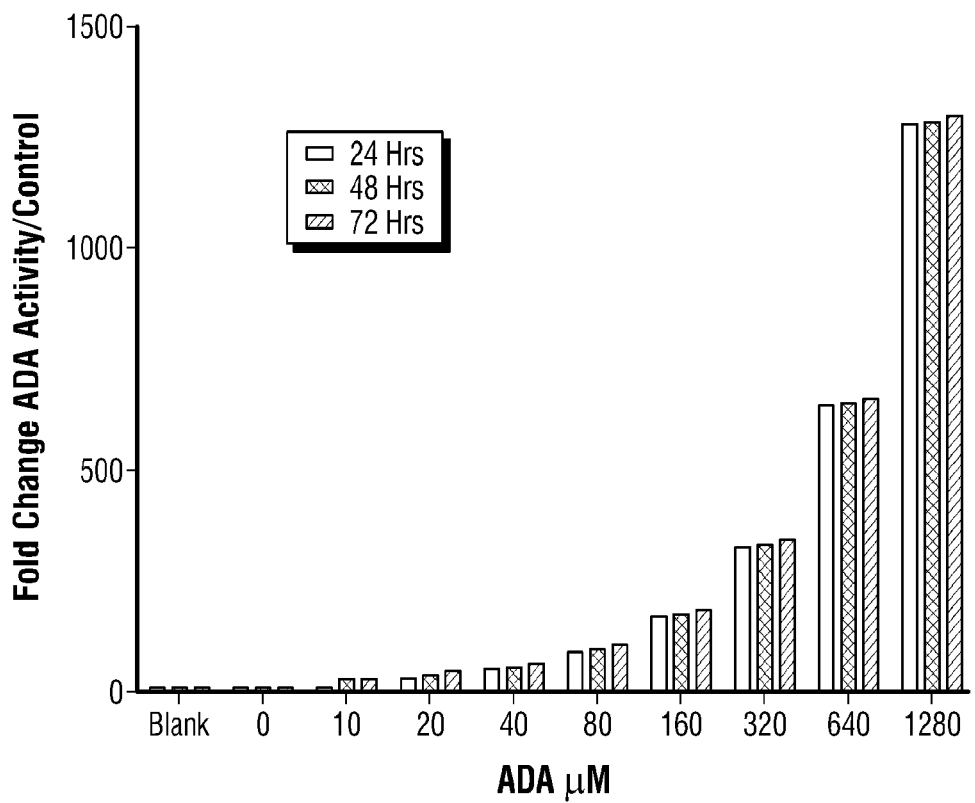
FIGS. 12A-12B show stability of mADA in cell culture medium at different time points (FIG. 12A) and estimation of enzyme activity of recombinant mADA-His and mADA-Fc (FIG. 12B).

4T1, MCF7 and T47D cells (1×10$^5$) were grown in 96 wells culture dish. 12 hrs later recombinant purified mADA at concentrations ranging from 0 µM-1280 µM was added to the culture medium of the tumor cells. The supernatant was collected after 24 h, 48 h and 72 h later and evaluated for ADA enzyme activity using a spectrophotometer and an Adenosine Deaminase Assay Kit at 550 nm Catalog Number: BQ 014-EALD. mADA retained its activity in cell culture medium even after 3 days (FIG. 12A).

Figure 12B:
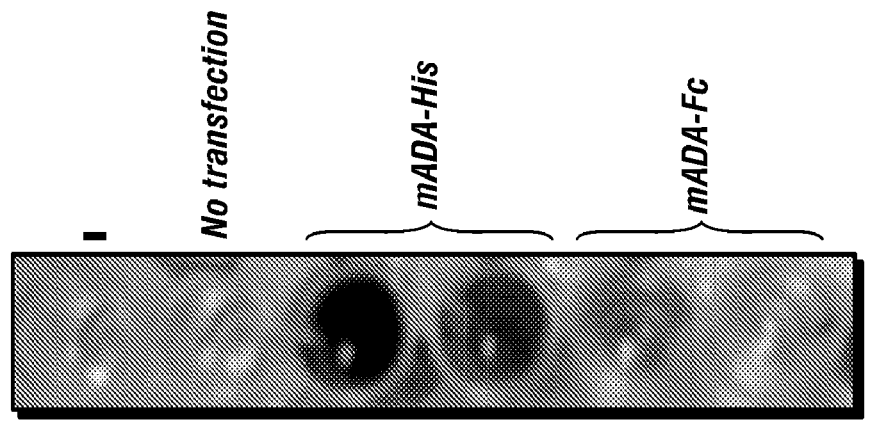

Enzyme activity of mADA-His and mADA-Fc was assayed with Adenosine Deaminase Assay Kit (BQ 014-EALD). Briefly the 180 µl of reagent 1 was added to 96-well plate. Followed by 5 µl of supernatant media obtained from HEK293F cells transfected with mADA-His or mADA-Fc. Later 90 µl of reagent was added to each well and incubated for 8 mins at 37° C. The OD was measured at 550 nm. Both mADA-His/Fc were enzymatically active in the supernatant (FIG. 12B).

Example 15

Wound Healing Assay

Figure 13B:
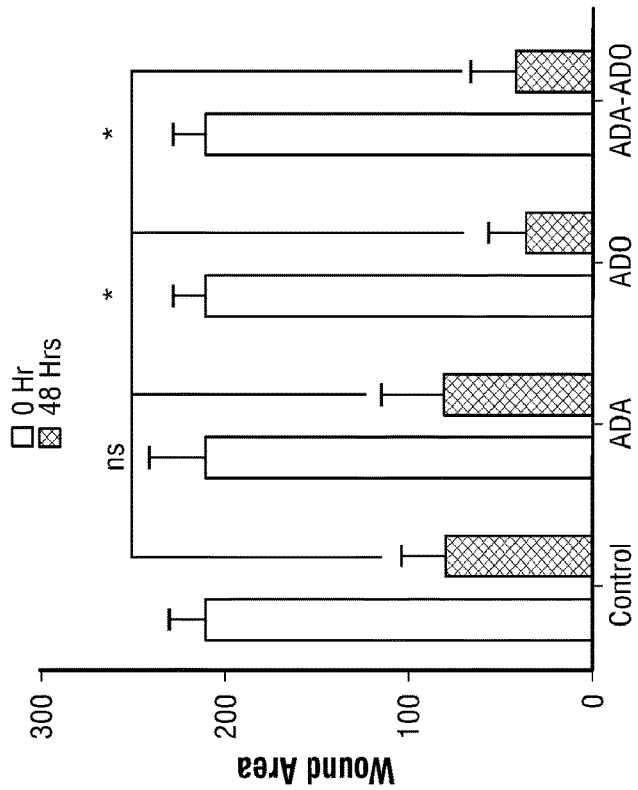
FIGS. 13A and 13B shows the effect of ADA and Ado on the wound healing ability of 4T1 cells. Ado marginally promoted wound healing in 4T1 cells. Addition of ADA did not alter the wound healing ability of 4T1 cells.
Figure 13A:
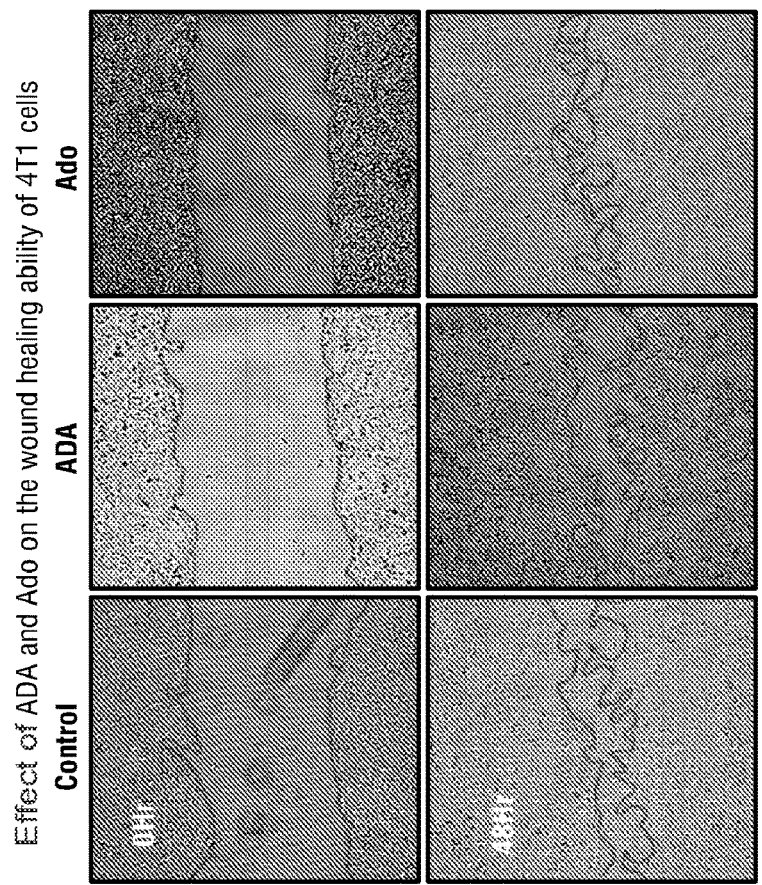

The effect of ADA and Ado on the wound healing ability of 4T1 cells was assessed. Briefly, 4T1 cells were cultured to confluence in 35 mm dishes in triplicates. 12 hrs later cell were rinsed with PBS and starved in low serum media (1.5 ml; 0.5%-0.1% serum in RPMI) overnight. Using a sterile 200 µl pipet tip, scratch wound was created on the cell surface 6) Cells were rinsed with PBS and replace with 1.5 ml of media containing any additives (10 µM Adenosine or 50 µM ADA or Both, one set of wells was kept without any additives. Pictures were taken immediately of the wound area in phase contrast and 10× and another at 48 hrs. Wound area was calculated using imagej and plotted. Ado marginally promoted wound healing in 4T1 cells. Addition of ADA did not alter the wound healing ability of 4T1 cells (FIG. 13A and FIG. 13B).

Example 16

Effect of cAdo on Cell Proliferation of HT29 Cells

Figure 14:
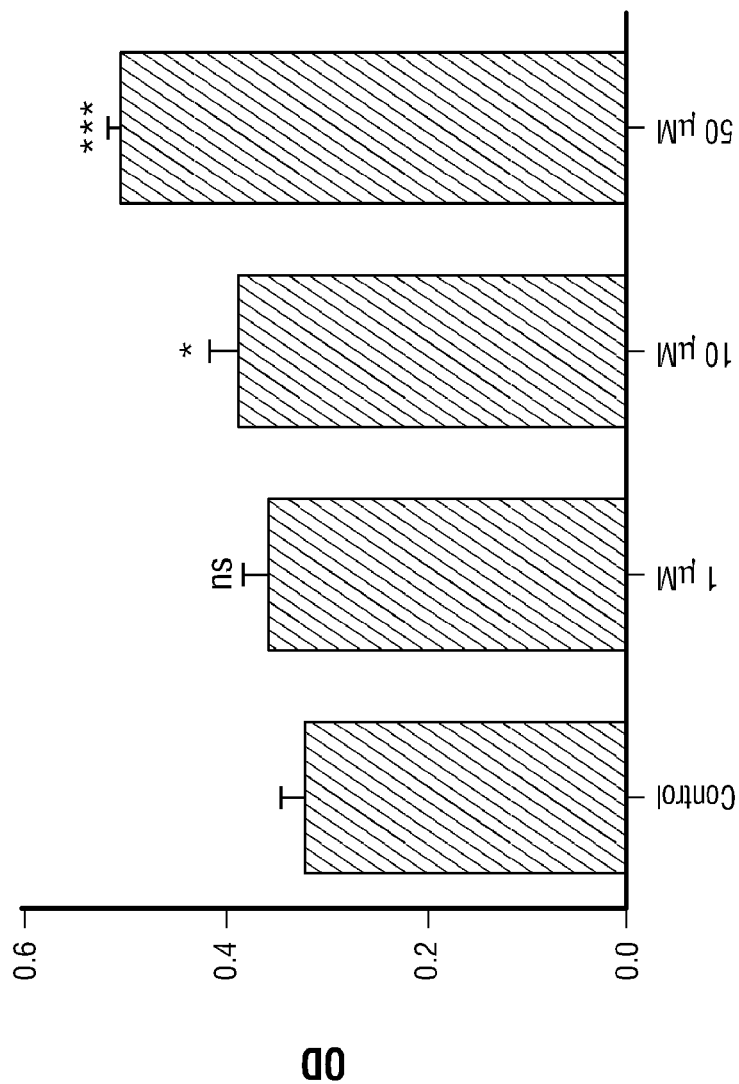
FIG. 14 shows effect of cAdo (2-chloro Ado) on cell proliferation of HT29 cells.

10$^4$ cells were seeded in 96 well dish in 100 µl. 12 hrs later the cells were treated with µM, 10 µM and 50 µM of cAdo and the cells were later assayed for cell number quantitatively using WST 1 reagent after 5 days. Briefly 10 µl of WST1 reagent was added to each well. The cells were incubated for 4 hrs. OD was measured using microtiter plate reader at 460 nm. The reference wavelength was ~650 nm. cAdo at concentrations of 10 µM and above showed a marginal increase in the rate of cell proliferation (FIG. 14).

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of activating an anti-tumor immune response for the treatment of a cancer in a tumor microenvironment of a solid tumor of a human subject comprising:
    detecting expression of at least one adenosine deaminase binding protein in the human subject in need thereof, wherein the adenosine deaminase binding protein is selected from a group consisting of CD26, A(1) adenosine receptors, and combinations thereof; and
    administering to the human subject a therapeutically effective amount of a composition comprising an adenosine deaminase isoenzyme 1 (ADA1) fusion protein, wherein the ADA1 fusion protein is fused to a targeting molecule that binds to a tumor associated antigen expressed in the tumor microenvironment of the solid tumor,
    wherein the ADA1 is a human ADA1,
    wherein the ADA1 fusion protein has the ability to simultaneously bind to A(1) adenosine receptors, CD26, and the tumor associated antigen in the tumor microenvironment of the solid tumor, and
    wherein the targeting molecule is a protein or a peptide.

2. The method of claim 1, wherein the ADA1 in the fusion protein is a purified human ADA1.

3. The method of claim 1, wherein the ADA1 in the fusion protein is a recombinant ADA1.

4. The method of claim 1, wherein the targeting molecule comprises the Fc portion of immunoglobulins.

5. The method of claim 4, wherein the immunoglobulins are IgG1 or IgG4 subtypes.

6. The method of claim 1, wherein the ADA1 fusion protein is comprised in nanoparticles.

7. The method of claim 1, wherein the method further comprises administering at least one other anti-cancer agent.

8. The method of claim 7, wherein the anti-cancer agent is selected from a group consisting of chemotherapeutic agents, radiotherapeutic agent, cytokines, anti-angiogenic agents, apoptosis-inducing agents, and anti-cancer immunotoxins.

9. The method of claim 1, wherein the cancer is the solid tumor.

10. The method of claim 9, wherein the solid tumor is selected from a group consisting of breast cancer, prostate cancer, bladder cancer, soft tissue sarcoma, lymphomas, esophageal cancer, uterine cancer, bone cancer, adrenal gland cancer, lung cancer, thyroid cancer, colon cancer, glioma; liver cancer, pancreatic cancer, renal cancer, cervical cancer, testicular cancer, head and neck cancer, ovarian cancer, neuroblastoma, and melanoma.

11. The method of claim 1, wherein the cancer is leukemia.

12. The method of claim 11, wherein the leukemia is selected from a group consisting of acute lymphocytic leukemia, chronic lymphocytic leukemia, acute myeloid leukemia, T cell leukemias, and B cell leukemias.

13. The method of claim 1, wherein the anti-tumor immune response comprises stimulation of T cell proliferation and activation of maturation of macrophages.

14. A method for targeted reduction of adenosine or deoxyadenosine in a tumor microenvironment of a solid tumor of a human subject comprising:
    detecting expression of at least one adenosine deaminase binding protein in the human subject in need thereof, wherein the adenosine deaminase binding protein is selected from a group consisting of CD26, A(1) adenosine receptors, and combinations thereof; and administering to the human subject a therapeutically effective amount of a composition comprising a polynucleotide encoding a adenosine deaminase fusion protein, wherein the polynucleotide encoding the fusion protein comprises:
- a first polynucleotide that encodes a targeting molecule, wherein the targeting molecule is a protein or a peptide; and
- a second polynucleotide that encodes adenosine deaminase isoenzyme 1 (ADA1), wherein the targeting molecule encoded by the first polynucleotide binds to a tumor associated antigen expressed in the tumor microenvironment of the solid tumor,
- wherein the ADA1 is a human ADA, and
- wherein the ADA1 fusion protein has the ability to simultaneously bind to A(1) adenosine receptors, CD26, and the tumor associated antigen in the tumor microenvironment of the solid tumor.

15. The method of claim 14, wherein the tumor associated antigen is selected from a group consisting of products of mutated oncogenes, products of tumor suppressor genes, products of mutated genes, overexpressed and/or aberrantly expressed cellular proteins, tumor antigens produced by oncogenic viruses, altered cell surface glycolipids and/or glycoproteins, and cell type-specific differentiation antigens.

16. The method of claim 14, wherein the tumor associated antigen is Her2/neu.

17. The method of claim 14, wherein the tumor associated antigen is selected from the group consisting of PD1, TIM-3, LAG-3, and CTLA4.

18. The method of claim 14, wherein the first polynucleotide and the second polynucleotide are operably linked via a third polynucleotide, wherein the third polynucleotide encodes a polypeptide linker between the targeting molecule and the ADA1.

19. The method of claim 18, wherein the polypeptide linker is a $(Gly_4Ser)_3$ peptide.

20. The method of claim 14, wherein the polynucleotide encoding the fusion protein is expressed by a vector.

21. The method of claim 14, wherein the targeted reduction of adenosine within the tumor microenvironment inhibits tumor growth, metastasis, and angiogenesis.

22. The method of claim 14, wherein the solid tumor is selected from a group consisting of breast cancer, prostate cancer, bladder cancer, soft tissue sarcoma, lymphomas, esophageal cancer, uterine cancer, bone cancer, adrenal gland cancer, lung cancer, thyroid cancer, colon cancer, glioma; liver cancer, pancreatic cancer, renal cancer, cervical cancer, testicular cancer, head and neck cancer, ovarian cancer, neuroblastoma, and melanoma.

23. The method of claim 21, wherein the adenosine deaminase fusion protein inhibits adenosine or deoxyadenosine within the tumor microenvironment.

24. The method of claim 23, wherein the inhibition of adenosine within the tumor microenvironment inhibits tumor growth, metastasis, and angiogenesis.

25. A method of treating a solid tumor in a tumor microenvironment of a human subject comprising:
- detecting expression of at least one adenosine deaminase binding protein in the human subject in need thereof, wherein the adenosine deaminase binding protein is selected from a group consisting of CD26, A(1) adenosine receptors, and combinations thereof; and
- administering to the human subject a therapeutically effective amount of a composition comprising a polynucleotide encoding a adenosine deaminase fusion protein, wherein the polynucleotide encoding the fusion protein comprises:
- a first polynucleotide that encodes a targeting molecule, wherein the targeting molecule is a protein or a peptide; and
- a second polynucleotide that encodes adenosine deaminase isoenzyme 1 (ADA1),
- wherein the targeting molecule encoded by the first polynucleotide binds to a tumor associated antigen expressed in the tumor microenvironment of the solid tumor,
- wherein the ADA1 is a human ADA1, and
- wherein the ADA1 fusion protein has the ability to simultaneously bind to A(1) adenosine receptors, CD26, and the tumor associated antigen in the tumor microenvironment of the solid tumor.

26. The method of claim 25, wherein the adenosine deaminase fusion protein binds CD26 on T cells to activate an anti-tumor immune response.

27. The method of claim 25, wherein the solid tumor is selected from a group consisting of breast cancer, prostate cancer, bladder cancer, soft tissue sarcoma, lymphomas, esophageal cancer, uterine cancer, bone cancer, adrenal gland cancer, lung cancer, thyroid cancer, colon cancer, glioma; liver cancer, pancreatic cancer, renal cancer, cervical cancer, testicular cancer, head and neck cancer, ovarian cancer, neuroblastoma, and melanoma.

28. A method of treating a solid tumor comprising:
- detecting expression of at least one adenosine-dependent pathway protein in a subject in need thereof, wherein the at least one adenosine-dependent pathway protein is selected from the group consisting of adenosine family of G-protein coupled receptors (GPCRs), A(1) adenosine receptors, A(2A) adenosine receptors, A(2B) adenosine receptors, A3 adenosine receptors, mitogen-activated protein kinases (MAPK), CD39, CD73, nucleoside transporters (NTs), ecto-adenosine deaminase, CD26, CD95, tumor necrosis factor receptor 1 (TNFR1), tumor necrosis factor-related apoptosis-inducing ligand receptor 2 (TRAILR2), Protein Kinase A (PKA), FAS-associated death domain protein (FADD), TNFR1-associated death domain protein (TRADD), BCL-2, cyclic AMP (cAMP), FLICE-inhibitory protein (FLIP), phosphorylated AKT, BAX, BAD, p53-upregulated modulator of apoptosis (PUMA), NOXA, and combinations thereof; and
- administering to the subject a therapeutically effective amount of a composition comprising a polynucleotide encoding a adenosine deaminase fusion protein, wherein the polynucleotide encoding the fusion protein comprises:
- a first polynucleotide that encodes a targeting molecule; and
- a second polynucleotide that encodes human adenosine deaminase isoenzyme 1 (ADA1),
- wherein the targeting molecule encoded by the first polynucleotide binds to a tumor associated antigen expressed in the tumor microenvironment of the solid tumor.

* * * * *